(12) United States Patent
Ang et al.

(10) Patent No.: US 12,216,822 B2
(45) Date of Patent: Feb. 4, 2025

(54) BIOPOTENTIAL-BASED GESTURE INTERPRETATION WITH MACHINE LABELING

(71) Applicant: Pison Technology, Inc., Boston, MA (US)

(72) Inventors: Dexter W. Ang, Boston, MA (US); David O. Cipoletta, Boston, MA (US)

(73) Assignee: Pison Technology, Inc., Boston, MA (US)

(*) Notice: Subject to any disclaimer, the term of this patent is extended or adjusted under 35 U.S.C. 154(b) by 0 days.

(21) Appl. No.: 18/047,023

(22) Filed: Oct. 17, 2022

(65) Prior Publication Data

US 2023/0113991 A1    Apr. 13, 2023

Related U.S. Application Data

(63) Continuation of application No. 17/404,075, filed on Aug. 17, 2021, now Pat. No. 11,474,604, which is a continuation of application No. 16/246,964, filed on Jan. 14, 2019, now Pat. No. 11,099,647, which is a continuation-in-part of application No. 16/055,777, filed on Aug. 6, 2018, now Pat. No. 10,627,914, which is a continuation of application No. 16/055,123, filed on Aug. 5, 2018, now Pat. No. 10,802,598.

(51) Int. Cl.
| | |
|---|---|
| G06F 3/01 | (2006.01) |
| G02B 27/01 | (2006.01) |
| G06F 3/16 | (2006.01) |
| H04W 4/80 | (2018.01) |

(52) U.S. Cl.
CPC ......... *G06F 3/015* (2013.01); *G02B 27/0172* (2013.01); *G06F 3/016* (2013.01); *G06F 3/017* (2013.01); *G06F 3/167* (2013.01); *H04W 4/80* (2018.02); *G02B 2027/0178* (2013.01)

(58) Field of Classification Search
CPC .......... G06F 3/015; G06F 3/016; G06F 3/017; G06F 3/167; G06F 1/163; G06F 3/0346; G06F 3/0484; G02B 27/0172; G02B 2027/0178; H04W 4/80; A61B 5/389; A61B 5/24; A61B 5/02438; A61B 5/0816; A61B 5/14542; A61B 5/7267; A61B 5/681
See application file for complete search history.

(56) References Cited

U.S. PATENT DOCUMENTS

| | | | |
|---|---|---|---|
| 9,448,636 B2 * | 9/2016 | Balzacki | A63F 13/213 |
| 10,497,191 B2 * | 12/2019 | Hyde | G07C 9/00563 |
| 10,593,137 B2 * | 3/2020 | Hyde | G07C 9/00563 |

(Continued)

*Primary Examiner* — William Lu
(74) *Attorney, Agent, or Firm* — Scale LLP

(57) ABSTRACT

System and methods for gesture-based control are described. In some embodiments, a system may include a wearable device having a biopotential sensor and a wrist motion sensor. The biopotential sensor may be configured to output a first data stream indicating actions of a person's hand. The system may further include a second device configured to output a second data stream, which may also indicate the actions of the person's hand. The system may be configured to analyze the first and second data streams to train a machine learning interpreter to classify actions of a person's hand based on at least biopotential data.

20 Claims, 14 Drawing Sheets

(56) References Cited

U.S. PATENT DOCUMENTS

Figure 1A:
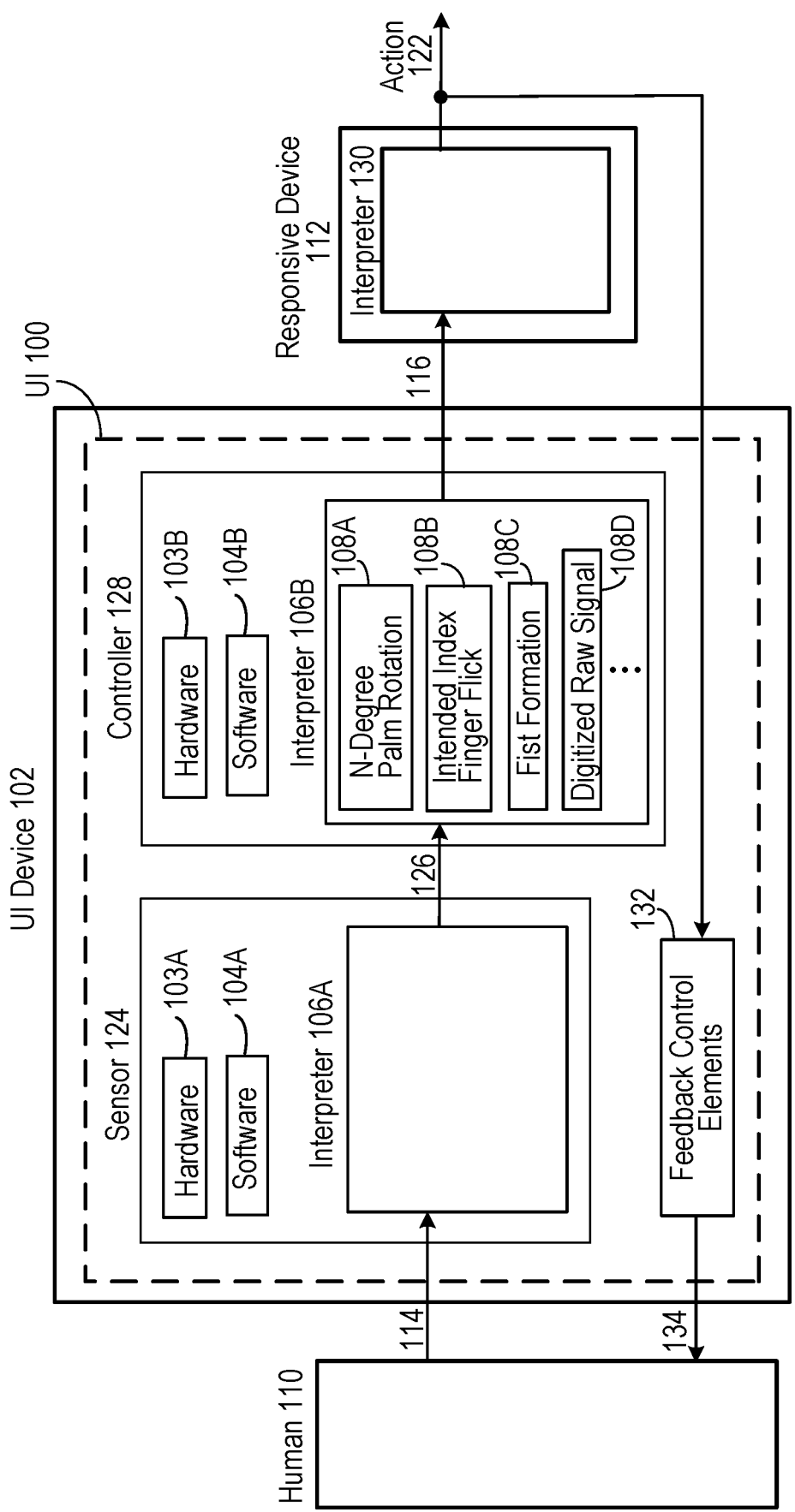

| Patent/Pub. No. | Date | Inventor | Classification |
|---|---|---|---|
| 10,722,165 B1* | 7/2020 | Douglas | A61B 5/163 |
| 10,790,054 B1* | 9/2020 | Vleugels | G16H 20/60 |
| 2005/0212767 A1* | 9/2005 | Marvit | G06F 1/1694 345/158 |
| 2009/0103780 A1* | 4/2009 | Nishihara | G06F 3/0425 382/103 |
| 2009/0265671 A1* | 10/2009 | Sachs | G06F 3/0346 715/863 |
| 2012/0188158 A1* | 7/2012 | Tan | G06F 3/015 345/156 |
| 2013/0138424 A1* | 5/2013 | Koenig | G10L 21/00 704/9 |
| 2013/0265229 A1* | 10/2013 | Forutanpour | G06F 3/015 345/158 |
| 2014/0028546 A1* | 1/2014 | Jeon | G06F 3/04842 345/156 |
| 2014/0282275 A1* | 9/2014 | Everitt | G06F 3/017 715/863 |
| 2015/0029092 A1* | 1/2015 | Holz | G06F 3/017 345/156 |
| 2015/0077326 A1* | 3/2015 | Kramer | G06F 3/0346 345/156 |
| 2015/0109202 A1* | 4/2015 | Ataee | G06F 3/015 345/156 |
| 2015/0163345 A1* | 6/2015 | Cornaby | G06F 3/002 345/633 |
| 2015/0312398 A1* | 10/2015 | Li | H04W 4/025 455/420 |
| 2017/0032281 A1* | 2/2017 | Hsu | G05B 19/41875 |
| 2017/0090583 A1* | 3/2017 | Zamora Esquivel | G06F 3/017 |
| 2017/0123487 A1* | 5/2017 | Hazra | G06F 3/0482 |
| 2017/0173262 A1* | 6/2017 | Veltz | G16H 20/17 |
| 2017/0185759 A1* | 6/2017 | Schmidt | G06F 21/32 |
| 2017/0220772 A1* | 8/2017 | Vleugels | A61B 5/0022 |
| 2018/0301140 A1* | 10/2018 | Turcott | G06N 3/044 |
| 2019/0011994 A1* | 1/2019 | Belfiori | G06F 18/2411 |
| 2019/0094981 A1* | 3/2019 | Bradski | H04N 21/414 |
| 2020/0042089 A1* | 2/2020 | Ang | G06F 3/016 |
| 2020/0182995 A1* | 6/2020 | Zeng | G01S 13/003 |
| 2020/0381101 A1* | 12/2020 | Vleugels | A61B 5/681 |

* cited by examiner

BIOPOTENTIAL-BASED GESTURE INTERPRETATION WITH MACHINE LABELING

CROSS-REFERENCE TO RELATED APPLICATIONS

This application is a continuation of U.S. patent application Ser. No. 17/404,075, filed Aug. 17, 2021 and issued as U.S. Pat. No. 11,474,604, which is a continuation of U.S. patent application Ser. No. 16/246,964, filed Jan. 14, 2019 and issued as U.S. Pat. No. 11,099,647, which is a continuation-in-part of Ser. No. 16/055,777, filed on Aug. 6, 2018 and issued as U.S. Pat. No. 10,627,914, which is a continuation of application Ser. No. 16/055,123, filed on Aug. 5, 2018 and issued as U.S. Pat. No. 10,802,598, the entire contents of all of which are incorporated herein by reference.

BACKGROUND

This description relates to user interface control of responsive devices.

A typical user interface (UI) enables interaction between a human and a responsive device by interpreting inputs from the human to generate outputs for the responsive device, by interpreting inputs from the responsive device to generate outputs for the human, or both. For example, one kind of user interface device is a keyboard that receives human keypresses (the inputs from the human) and interprets them to generate key codes as outputs for responsive devices like computers. Another example of a user interface device is a computer mouse with haptic feedback that receives signals indicating an alert from a computer (the responsive device), such as the arrival of an incoming message (the inputs from the responsive device), and interprets the signals to generate vibrations as outputs for the human.

SUMMARY

In general, in an aspect, first signals are received representing manipulation of a physical feature of a physical device by one or more fingers of a hand of a user. Second signals are received representing tissue electrical activity indicative of and occurring prior to the manipulation. The first signals and the second signals are processed to identify the occurrence of the manipulation. A control signal is sent to a game or other application with which the user is interacting. The control signal corresponds to the identified occurrence of the manipulation.

Implementations may include one or a combination of two or more of the following features. The manipulation of the physical feature and the tissue electrical activity indicative of the manipulation occur at different times. The processing of the first signals and the second signals includes determining which of the manipulation of the physical feature and the tissue electrical activity more accurately represents the occurrence of the manipulation. The processing of the first signals and the second signals includes determining that the earlier of the manipulation of the physical feature in the tissue electrical activity more accurately represents the occurrence of the manipulation. The sending of the control signal to a game or other application includes posting an event to an event queue of an operating system associated with the game or the other application. The processing of the first signals and the second signals includes applying the first signals and the second signals to a classifier.

The training of the classifier is based on first signals representing manipulations of the physical feature and second signals representing tissue electrical activities. The training of the classifier includes training the classifier repeatedly while the user is interacting with the game or other application. The training of the classifier includes applying a dedicated calibration routine before the user begins to interact with the game or other application. Instructions are received from the user about the training of the classifier. The processing of the first signals and the second signals includes applying the first signals and the second signals to a selected classifier among a set of classifiers. The selected classifier is selected based on input of the user. The tissue electrical activity corresponds to a contraction or extension or both of a muscle of the user.

The physical device includes a physical mouse and the physical feature includes a button or switch of the mouse. The manipulation includes a mouse click. The tissue electrical activity occurs at the anterior side of the wrist of the user. A signal is received indicative of a state of physical contact between the user and the physical device, and the processing the first signals and the second signals to identify the occurrence of the manipulation includes taking account of the signal indicative of the state of physical contact. The first signals are received as a stream of samples. The second signals are received as a stream of samples. The first signals or the second signals or both our time stamped. Two or more channels of the second signals are received. Third signals are received from sensors facing the posterior wrist on the radial side of the user. The second signals are received from sensors belonging to a tattoo-based or sticker-based component. The second signals are received from a user interface device. The second signals are received from implanted sensors.

The second signals are received from sensors on a watch. The physical device and the user interface device are electrically coupled. The physical device and the user interface device are mechanically coupled. The classifier is customized for a context in which the game or other application is used. The context includes the model or particular unit of the model of the physical device. The context includes the identity of the user. The context includes the behavior of the user interface device. The context includes style of manipulation by the user. The effectiveness of the use of the user interface device by the user is measured. Information about the first signals, the second signals, the physical device, the processing of the first signals and the second signals, or the sending of the control signal to the game or other application, or combinations of two or more of those his reported to the user. A signal is received representing a position or orientation of the hand of the user relative to the physical device. The characteristics of the manipulation are determined based on the first signals or the second signals or both. The characteristics include the forcefulness of the manipulation. The characteristics include identities of one or more fingers involved in the manipulation. The characteristics include wrist rotations. Third signals are received from an IMU and the processing takes account of the third signals from the IMU.

In general, in an aspect, a user interface device has a sensor configured to detect, at a wrist of a human, nerve or other tissue electrical signals associated with an intended contraction of a muscle to cause a rapid motion of a finger. An output provides information representative of the nerve or other tissue electrical signals associated with the intended contraction of the muscle to an interpreter of the information.

Implementations may include one or a combination of two or more of the following features. The interpreter is configured to interpret the information representative of the nerve or other tissue electrical signals and provide an output indicative of the intended contraction of the muscle to cause the rapid motion of the finger. A responsive device is coupled to the interpreter and configured to respond to the intended contraction of the muscle by an action. The responsive device is configured to respond by an action that includes changing an audio or visual presentation to the human. The rapid motion of the finger includes a flick of the finger. The responsive device is configured to respond by an action that includes changing the audio or visual presentation as if the intended contraction of the muscle corresponded to an invocation of a user interface control. The user interface device includes the interpreter. The rapid motion of the finger has a duration less than one-half second. The rapid motion of the finger includes a contraction and an extension of the finger. The contraction and extension are repeated. The flick of the finger includes a flick up of an index finger.

In general, in an aspect, a user interface device has a sensor configured to detect, at a wrist of a human, nerve or other tissue electrical signals associated with an intended contraction of a muscle to cause a rotation of a part of the human. An output carries information representative of the nerve or other tissue electrical signals associated with the intended contraction of the muscle to an interpreter of the information.

Implementations may include one or a combination of two or more of the following features. The interpreter is configured to interpret the information representative of the nerve or other tissue electrical signals and provide an output indicative of the intended contraction of the muscle to cause the rotation. A responsive device is coupled to the interpreter and configured to respond to the intended contraction of the muscle by an action. The responsive device is configured to respond by an action that includes changing an audio or visual presentation to the human. The rotation includes a rotation of a palm relative to an elbow. The responsive device is configured to respond by an action that includes changing the audio or visual presentation as if the intended contraction of the muscle corresponded to manipulation of a displayed graphical element. The manipulation of the displayed graphical element includes rotating the displayed graphical element. The displayed graphical element includes a three-dimensional representation of an object and the manipulation of the displayed graphical element includes rotating the displayed graphical element in three-dimensional space. The displayed graphical element includes a digital camera control and the manipulation of the displayed graphical element includes adjusting the digital camera control. The displayed graphical element includes characters of an access code and the manipulation of the displayed graphical element includes rotating the displayed graphical element to select characters of the access code. The user interface device includes the interpreter. The rotation has an angular extent within a range of −180° to 180°.

In general, in an aspect, a user interface device has a sensor configured to detect, at a wrist of a human, nerve or other tissue electrical signals associated with an intended contraction of a muscle to cause a stationary hold of a part of the human. An output carries information representative of the nerve or other tissue electrical signals associated with the intended contraction of the muscle to an interpreter of the information.

Implementations may include one or a combination of two or more of the following features. The interpreter is configured to interpret the information representative of the nerve or other tissue electrical signals and provide an output indicative of the intended contraction of the muscle to cause the stationary hold. A responsive device is coupled to the interpreter and configured to respond to the intended contraction of the muscle by an action. The responsive device is configured to respond by an action that includes changing an audio or visual presentation to the human. The stationary hold includes the human holding a hand in a position. The stationary hold includes a part of the human held in a position at the end of another intended contraction of the muscle to cause a motion of the part of the human. The responsive device is configured to respond by an action that includes continuing a change of the audio or visual presentation until the stationary hold ends. The other intended contraction of the muscle is to cause a rotation of the part of the human and the stationary hold includes the part of the human being held in a position during or at the end of the rotation. The other intended contraction of the muscle is to cause an index finger lift and the stationary hold includes the finger being held in a position during or at the end of the rotation. The responsive device is configured to respond to the stationary hold by locking the responsive device or unlocking the responsive device. The sensor is configured to detect another intended contraction of the muscle, the other intended contraction of the muscle to cause a flick of a finger. The interpreter and in which the interpreter is configured to interpret the information representative of the nerve or other tissue electrical signals and to provide an output indicative of the combination of the intended contraction and the other intended contraction. The responsive device is configured to respond by an action that includes changing the audio or visual presentation as if the intended contraction of the muscle corresponded to a locked or unlocked state of an application being executed on the responsive device. The user interface device includes the interpreter. The user interface of claim including a controller that is at least partly in the user interface device. The user interface of claim in which the controller is at least partly in a responsive device.

In general, in an aspect, a user interface device has a sensor configured to detect nerve or other tissue electrical signals associated with an intended contraction of a muscle to cause a motion of a part of a human. An output provides information representative of the nerve or other tissue electrical signals associated with the intended contraction of the muscle to cause an action by a responsive device. A feedback component is configured to provide feedback to the human indicative of the action by the responsive device.

Implementations may include one or a combination of two or more of the following features. The feedback component is part of the user interface device. The feedback component includes a haptic element configured to provide haptic feedback to the human. The feedback component provides information to enable the human to control an intended contraction of the muscle in accordance with the feedback. The feedback component is configured to receive feedback information from the responsive device. The responsive device includes the feedback component. The responsive device includes smart glasses. The feedback includes a visible element displayed by the smart glasses. The feedback includes an element displayed by the responsive device. The feedback includes a sound produced by the responsive device.

In general, in an aspect, an apparatus includes two or more user interface devices. Each of the user interface devices has a sensor to detect an input from a human. An output carries information representative of the input to an interpreter of the information. A first one of the user interface devices has a sensor configured to detect, at a wrist of a human, nerve or other tissue electrical signals associated with an intended contraction of a muscle. An output carries information representative of the nerve or other tissue electrical signals associated with the intended contraction of the muscle to an interpreter of the information. An interpreter is configured to generate an interpreted output based on a combination of the output of the first one of the user interface devices and an output of another one of the user interface devices.

Implementations may include one or a combination of two or more of the following features. A responsive device is configured to take an action in response to the interpreted output. Two or more of the user interface devices have sensors configured to detect, at a wrist of the human, nerve or other tissue electrical signals associated with intended contraction of two or more muscles. The sensor of one of the user interface devices includes an inertial measurement unit (IMU). The inertial measurement unit is calibrated using a calibration technique. The inertial measurement unit is configured to access a value corresponding to a reference point. The reference point is independent of the position of the inertial measurement unit. A vector provided by the inertial measurement unit is compared to a second vector that is calculated using the value corresponding to the reference point. The calibration technique is performed after a predefined number of spatial calculations of the inertial measurement unit. The calibration technique is performed in response to a command from the human. There are two or more responsive devices configured to take respective actions in response to the interpreted output of at least one of the user interface devices. Two of the user interface devices are wrist-worn user interface devices. At least two of the user interface devices have sensors to detect inputs from a single human. At least two of the user interfaces devices are worn by different humans and are wrist-worn devices.

In general, in an aspect, a user interface device has a sensor to detect nerve or other tissue electrical signals associated with an intended contraction of a muscle to cause a motion of a part of a human. An output provides information representative of the nerve or other tissue electrical signals associated with the intended contraction of the muscle to cause an action by a responsive device. The information provided at the output includes raw data representing the nerve or other tissue electrical signals. The output provides the information to an interpreter external to the user interface device and is configured to interpret the raw data for use in causing the action by the responsive device.

Implementations may include one or a combination of two or more of the following features. The output is coupled to the responsive device. The output is coupled to a communication channel that is also coupled to the responsive device. The communication channel includes a mesh network. The output is coupled to an intermediary device that is also coupled to the responsive device. The output is coupled to a socket. The output is coupled to a distribution system to distribute the output to responsive devices located at distances from the user interface device greater than can be reached by Bluetooth communications.

In general, in an aspect, a user interface device has a sensor to detect nerve or other tissue electrical signals associated with an intended contraction of a muscle to cause a motion of a part of a human. An output provides information representative of the nerve or other tissue electrical signals associated with the intended contraction of the muscle to cause an action by a responsive device. The output is coupled to a distribution system to distribute the output to responsive devices located at distances from the user interface device greater than can be reached by Bluetooth communications.

Implementations may include one or a combination of two or more of the following features. The output is coupled to the distribution system through a socket. The output is coupled to a mesh network.

In general, in an aspect, a user interface device has a sensor configured to detect, at a wrist of a human, nerve or other tissue electrical signals associated with an intended contraction of a muscle to cause a motion of a part of a human. An output provides information representative of the nerve or other tissue electrical signals associated with the intended contraction of the muscle to an interpreter of the information.

Implementations may include one or a combination of two or more of the following features. There is a controller. The controller is at least partly in the user interface device. The controller is at least partly in a responsive device. The controller is configured to effect an action by a responsive device. The controller is configured to effect the action by altering a presentation by the responsive device. The controller is configured to alter the presentation by unlocking one or more of the responsive devices. The controller is configured to alter the presentation with respect to a scrolling function. The controller is configured to alter the presentation by presenting a selection. The controller is configured to alter the presentation by presenting a home screen. The controller is configured to alter the presentation by providing a visual or audible indication of an output of the controller. The visual or audible indication includes at least one of a change of color, a flashing, a change of size, a change of shape, a change of appearance, or a combination of any two or more of them. The controller is configured to generate an output that unlocks a functionality of a responsive device. The controller is configured to cause the responsive device to navigate a menu. The controller is configured to cause the responsive device to perform a selection. The controller is configured to cause the responsive device to perform a zoom. The zoom alters a presentation including a display. The controller is configured to cause the responsive device to capture an image, video, or a sound, or a combination of them. The selection is performed on alphanumerical characters. The responsive device is configured to operate compatibly with a peripheral device that can generate an output for controlling the action of the responsive device. The controller is configured to cause the responsive device to perform an action that can also be caused by the output generated by the peripheral device. The controller is configured not to control the action of the responsive device unless the human is in contact with the peripheral device. The peripheral device includes a handheld peripheral device. The action of the responsive device is controlled without the human touching the responsive device. The controller is configured to send the output to the responsive device based on a Bluetooth round robin. An intermediary routing device manages connections with the responsive device. The controller is configured to send the output to the responsive device through the intermediary routing device. The responsive device is configured to provide a presentation to a user of the user interface device. The presentation includes a display or sound or both. A second user interface device is configured to detect additional nerve or other tissue electrical signals of a human and generate data representative of the additional nerve or other tissue electrical signals. One or more interpreters are configured to make interpretations of the data representative of the additional nerve or other tissue electrical signals. The controller is configured to generate the output based on a joint consideration of the interpretations of the data representative of the nerve or other tissue electrical signals and the interpretations of the data representative of the additional nerve or other tissue electrical signals. The controller is configured to generate the output based on a separate consideration of the interpretations of the data representative of the nerve or other tissue electrical signals and the interpretations of the data representative of the additional nerve or other tissue electrical signals. The controller is configured to generate the output based on audio input. The controller is configured to send the output with a time delay. The time delay corresponds to a time required for interpretation of the data representative of the nerve or other tissue electrical signals. The nerve or other tissue electrical signals of the human detected by the sensor correspond to one or more gestures or intended gestures. The nerve or other tissue electrical signals of the human detected by the sensor correspond to one or more motions or intended motions of the human. The one or more interpreters are configured to provide one or more interpretations indicative of the one or more motions or intended motions of the human. The one or more motions or intended motions of the human include one or more muscle contractions or extensions in an upper extremity of the human.

In general, in an aspect, a user interface device has a sensor configured to detect, at a wrist of a human, signals indicative of a unique identity of the human, and an output to provide information representative of the signals to an interpreter of the information for use in determining the unique identity of the human.

Implementations may include one or a combination of two or more of the following features. An authentication system generates a verification output with respect to an identity of the human based on the provided information. The authentication system is configured to control the human's access to a responsive device based on the verification output. The provided information includes biometric signal data and the verification output is based on the biometric signal data. The biometric signal data includes nerve or other tissue electrical activity sensed at the surface of the skin of the wrist. The biometric signal data is indicative of wrist acceleration, wrist orientation, or other motion or position of the wrist of the human. The biometric signal data is provided during a passive mode of the user interface device. The biometric signal data is provided during an active mode of a responsive device being controlled by the human through the user interface device. The verification output is generated repeatedly at successive times. The verification output is generated continuously.

These and other aspects, features, and implementations (a) can be expressed as methods, apparatus, systems, components, program products, methods of doing business, means or steps for performing a function, and in other ways, and (b) will become apparent from the following descriptions, including the claims.

DESCRIPTION

FIGS. 1A, 1B, 3, 9, 10 and 14 are block diagrams.
FIGS. 2, 4, 5, 6A, 6B, 7A, 7B, 8, and 13 are schematics.
FIGS. 11 and 12 are user interface displays.
Here we describe, among other things, features of user interfaces, in some cases features that rely on detected tissue electrical signals (in some cases, nerve or other tissue electrical signals) to be interpreted to generate outputs for the responsive device. User interfaces that rely on nerve or other tissue electrical signals can require less hardware to implement, can be operated by a wider range of people, and can be more intuitive than typical user interfaces, among other advantages. A variety of user interface techniques for controlling responsive devices (and applications running on them) can be implemented based on such user interfaces, including user interface techniques not possible or difficult to implement using typical user interfaces.

We use the term "responsive device" broadly to include, for example, any combination of hardware components or software components or both that is capable of performing one or more specific actions in response to receiving a corresponding signal (e.g., an input signal or an output signal generated for, sent to, or received by the responsive device). Examples of responsive devices include, but are not limited to, computers, mobile phones, smart glasses, smartwatches, health and fitness monitors, smart speakers, smart lights, smart thermostats, smart home devices, virtual reality headsets, televisions, audio systems, cameras, repeaters, nodes in a mesh network, application programming interfaces (APIs) and other devices, and combinations of them. In some cases, a responsive device may comprise multiple responsive devices acting in parallel or in a chain or both. For example, a node in a mesh network (itself a responsive device), upon receiving a signal, may repeat or forward the signal (an action) to one or more other nodes (each of which can also be considered a responsive device and at which an action is taken). In this example, each individual node can be considered a responsive device because it performs an action in response to receiving a corresponding signal. In some cases, two or more responsive devices can perform actions in parallel in response to signals from one or more user interface devices. In some instances, a responsive device can perform one or more actions in response to two or more signals from two different user interface devices.

We use the term "action" broadly to include any function or combination of functions capable of being performed at, by, or on behalf of a responsive device. Examples of actions include powering the responsive device, performing a mouse click, scrolling, exiting a program, controlling presented user interface controls and other elements, adjusting a volume level, transmitting a signal, and saving data, among a wide variety of others, and combinations of them.

We use the term "user interface" broadly to include, for example, a conceptual technology or capability that can be implemented in any combination of hardware components or software components and can interpret one or more inputs from a human to generate one or more outputs for a responsive device, can interpret one or more inputs from a responsive device to generate one or more outputs for a human, or can do both. A user interface can take on or be implemented in various physical forms or combinations of physical forms. In some cases, a combination of components that comprises a user interface can be located physically in a discrete "user interface device" that is distinct from the human and from the responsive device.

We use the term "user interface device" broadly to include any one or more hardware or software components or devices that together at least partially implement or provide a user interface by serving as an intermediary between a human and one or more responsive devices. For example, a keyboard is a discrete user interface device containing components that interpret human keypresses (the inputs from the human) to generate key codes as outputs for responsive devices like computers. Examples of user interface devices include a keyboard, a mouse, a trackball, a trackpad, smart glasses, wrist worn devices, clickers, augmented reality and virtual reality controllers, and head-tracking devices, among a wide variety of others, and combinations of them.

In some cases, a device may simultaneously be considered both a user interface device and a responsive device. For example, a smart watch can be considered a user interface device because it can serve as an intermediary between a human and a responsive device such as a smart television. The smart watch can also be considered a responsive device because upon receiving an input signal representative of a human touch, the smart watch can itself perform actions such as opening an email or sending control signals to other smart devices.

In some cases, the combination of components that comprises the user interface can be physically located entirely within the responsive device, without the need of a distinct user interface device to serve as an intermediary. For example, in some cases, a television can be operated without the need of a remote (user interface device) to serve as an intermediary between the user (human) and the television (responsive device). In this example, the human can operate the television (responsive device) directly by pressing buttons on the television because the user interface is entirely located within the responsive device. Similarly, a combination of components that comprise a responsive device can be physically located entirely within a user interface device.

In some cases, the combination of components that comprises the user interface can be physically located within two or more discrete user interface devices, two or more responsive devices, or a combination of one or more discrete user interface devices and one or more responsive devices.

In some cases, a user interface may include one or more interpreters that perform one or more interpretation steps in order to interpret one or more inputs from one or more humans to generate one or more outputs for one or more responsive devices. In some implementations, each of the interpreters may interpret inputs from a responsive device to generate an output for a human. Or each of the interpreters may perform both interpretations of inputs from one or more humans and interpretations of inputs from a responsive device. For example, a user interface may include a first interpreter to interpret biological inputs (such as nerve or other tissue electrical signals) from a human to generate electrical signals or data representative of the biological inputs from the human. In some cases, biological inputs from the human can include biological signals indicative of vital signs or physical exercise such as heart rate, respiratory rate, skin capacitance, oxygen saturation of blood, a number of steps taken, or a number of calories burned, among other things. The user interface may include a second interpreter (i.e., in series with the first interpreter) to interpret the generated electrical signals or data representative of the biological inputs from the human to generate a corresponding output (such as a control output) for the responsive device. In some instances, elements of an interpreter can be distributed among one or more user interface devices or one or more responsive devices, or combinations of them.

We use the term "interpret" broadly to include, for example, any determination of one or more outputs that depends on, corresponds to, is based on, translates, maps, transforms, or is determined by one or more received inputs. In some cases, interpretation is performed at a low-level, with the determined outputs being substantially similar to the received inputs. For example, a sensing circuit that outputs digitized or compressed electrical signals or data corresponding to received biological inputs is said to "interpret" the biological inputs. In some cases, interpretation comprises determining a binary output dependent on whether or not an aggregate amount of received biological inputs is greater than a threshold amount, without requiring the classification of the inputs as a specific gesture. In some cases, interpretation is performed at a higher level such as a classifier (interpreter) used to classify (interpret) the inputs as an interpretation selected from among a set of possible interpretations before generating an output corresponding to the selected interpretation. For example, an interpreter that receives as inputs IMU signals from a wrist-worn user interface device may classify the signals as an "N-Degree Palm Rotation" interpretation and generate a corresponding output signal for a computer (a responsive device) to use in controlling an element presented on a display of the computer. In some cases, multiple interpretations of corresponding inputs may be aggregated by a controller to generate an output signal corresponding to the aggregated interpretations. In both of these examples, the interpreter is said to "interpret" the IMU signals. Interpretations can be characterized by a wide variety of factors. For example, interpretations can include actions, motions, sounds, gestures, intentions, eye movements, actions associated with responsive devices (such as a mouse click or a keyboard keypress, to name just two), physical activities, static holds, pauses, digitized raw signals, compressed raw signals and others.

As shown in FIG. 1A, an example user interface 100 can be implemented in hardware components 103A, 103B and software components 104A, 104B. The software components include machine readable instructions stored in memory or storage (which can be part of the hardware 103A, 103B) and executable by one or more processors (which also can be part of the hardware 103A, 103B). When executed by a processor the instructions can effect one or more interpretations of one or more inputs 114 from one or more humans 110 to generate one or more outputs 116 for one or more responsive devices 112. In the configuration depicted in FIG. 1A, the user interface 100 is physically implemented entirely within a discrete self-contained user interface device 102 that is distinct from the human 110 and the responsive device 112.

A wide variety of inputs 114 can be provided by the human 110 including electrical signals, motions of parts of the body, thermal inputs, perspiration, sounds, breath, and other physiological actions (voluntary and involuntary). In some examples, the inputs can include nerve and other tissue electrical signals and other biological signals that can be detected by one or more sensors (e.g. sensor 124) that are placed on or near the human. In some examples, the inputs can include electromyography (EMG) signals collected at, or directly above, the site of a muscle, morphed EMG signals that have propagated through the body from a source to a propagation site distinct from the site of the muscle or the skin directly above it, motion artifacts from tendon movement, or any combination of them (e.g. in a bulk signal). In some cases, the inputs can include biological signals indicative of vital signs or physical exercise such as heart rate, respiratory rate, skin capacitance, oxygen saturation of blood, a number of steps taken, or a number of calories burned, among other things.

We use the term "sensor" broadly to include, for example, any device that can sense, detect, or measure a physical parameter, phenomenon, or occurrence. Examples of sensors include IMUs, gyroscopes, moisture sensors, temperature sensors, visible light sensors, infrared sensors, cameras, audio sensors, proximity sensors, ultrasound sensors, haptics, skin impedance pressure sensors, electromagnetic interference sensors, touch capacitance sensors, external devices and other detectors, and combinations of them.

In our discussion, we often use, as an example, user interfaces that receive, at least in part, nerve or other tissue electrical signals that are detected at the wrist by electrical sensors. In some cases, the electrical sensors are located at a posterior aspect of the wrist (e.g. the top of the wrist), allowing for incorporation of the sensors into watches, fitness trackers, and other devices having rigid or flexible bodies. In some cases, having the electrical sensors at only the posterior aspect of the wrist can obviate the need for distributing the sensors circumferentially around the wrist, such as in a wrist strap or bracelet. Technologies for detecting and using nerve or other tissue electrical signals or other tissue electrical signals at any part of the body, especially the wrist, are described in U.S. application Ser. No. 15/826,131, filed on Nov. 29, 2017, the entire contents of which are incorporated here by reference.

In the example of FIG. 1A, the user interface device 102 includes two interpreters 106A, 106B. The first interpreter 106A is included in the sensor 124 and is implemented using a combination of hardware components 103A and software components 104A. The first interpreter 106A receives biological inputs 114 (such as nerve or other tissue electrical signals) from the human 110 and interprets them to generate electrical signals or data 126 representative of the biological inputs 114. In this example, the second interpreter 106B is included in a controller 128 and is implemented using a combination of hardware components 103B and software components 104B. The second interpreter 106B receives the electrical signals or data 126 representative of the biological inputs 114 from the human 110 and interprets them. In order to interpret the electrical signals or data 126, the second interpreter 106B stores information about possible interpretations 108A-D. Upon receiving the electrical signals or data 126, the second interpreter 106B classifies the electrical signals or data 126 as corresponding to one of the interpretations among the possible interpretations 108A-D. The controller 128 aggregates the interpretations made by the second interpreter 106B and generates an output 116 for the responsive device 112 depending on a variety of contextual factors including, but not limited to, the timing of the interpretations, the type of responsive device 112, and an operational status of the responsive device, or combinations of them, among other things.

In examples discussed here, interpretations may include identified gestures or identified intentions for gestures. For example, based on electrical signals 126 generated by an IMU sensor 124, the second interpreter 106B may classify the signals 126 as corresponding to an "N-Degree Palm Rotation" gesture 108A. Similarly, based on electrical signals 126 generated by an electroneurography (e.g., nerve or other tissue electrical signal) sensor 124, the second interpreter 106B may classify the signals 126 as an "Intended Index Finger Flick Up" gesture 108B. Another interpretation could be a "fist formation" 108C. Interpretations may also be lower-level. For example, based on electrical signals 126 generated by the first interpreter, the second interpreter 106B may simply interpret the signals as "Digitized Raw Signal" 108D and generate an output 116 that is similar in its level of abstraction to the raw electrical signals 126.

Classifying the electrical signals 126 as corresponding to an interpretation selected from the interpretations 108A-D can be done using a variety of classification techniques. For example, in some cases, classification (interpretation) of nerve or other tissue electrical signals (our data corresponding to the signal) as an "Intended Index Finger Flick Up" gesture can be implemented using a single threshold value. The average voltage amplitude of gestures can be used to train and select generic threshold values manually or automatically through machine learning or other algorithms. In some cases, classification can involve signal processing of the electrical signals 126 and the implementation of techniques such as logistic regression, decision trees, support vector machines, or neural networks. In some cases, accurate classification of the electrical signals 126 can be performed without requiring a user to complete a dedicated calibration process prior to operating the user interface device 102. For example, the second interpreter 106B may include a general classifier that is satisfactorily accurate for most people without the need for personalized calibration prior to operation of the user interface device 102. In some cases, personalization of the general classifier (e.g. by tuning parameters of the general classifier) can be performed in real time as the user operates the user interface device 102.

A wide variety of other interpretation techniques can be applied in addition to or other than classification. For example, machine learning techniques using features such as entropy, root-mean square, average value, frequency-based analysis, pattern matching, log detect, spatial analysis from multiple electrode channels, sensor fusion with IMU and other inputs, time-variance of user behavior, slope of amplitude changes, and duration and shape of waveforms can be applied, among other things.

After classifying the electrical signals or data 126 as an interpretation selected from the interpretations 108A-C, the user interface device 102 can then send to a responsive device 112 an output 116 corresponding to the classified interpretation. Outputs 116 for the responsive device 112 can include data or commands for controlling actions 122 of the responsive device 112. Outputs 116 can also include raw digitized information for a responsive device 112 to utilize as it wishes.

More generally, outputs for the responsive device can comprise a wide variety of forms and modes. For example, outputs can be in the form of electrical signals, data, commands, instructions, packets, electromagnetic waves, sounds, light, and combinations of them, among others. Outputs can conform to a wide variety of standard or proprietary communication protocols.

The responsive device 112 may include an interpreter 130 for interpreting the output 116 in order to perform a corresponding action 122. Upon receiving the output 116 for the responsive device 112, the responsive device 112 interprets the output 116 and performs the corresponding action 122. The action can comprise a wide variety of forms and modes. An action can include a physical motion, a sound, a display, a light, or a presentation or manipulation of textual, graphical, audiovisual or other user interface elements on a display device, or combinations of them, among other things.

The user interface 100 of FIG. 1A can be configured to operate as an open control loop or a closed control loop. In an open control loop, the action 122 performed by the responsive device 112 does not provide feedback to the user that directly influences the human's inputs. However, as discussed previously, a user interface may be capable not only of receiving inputs from a human to generate outputs for a responsive device, but may also receive inputs from the responsive device to generate outputs for the human. In some cases, it is possible for a user interface to include closed loop control, using feedback control elements 132.

For example, consider a mouse a with a haptic feedback element. The mouse is a user interface device 102 that receives motion and clicking inputs 114 from a human 110 and interprets the inputs to generate a command (output 116) for a computer (responsive device 112) to move a cursor or perform a mouse click (action 122). Depending on contextual factors, in response to receiving a mouse click command (output 116), the computer (responsive device 112) may send a vibration command (action 122) to the mouse (the user interface device 102). The vibration command can be interpreted and acted upon by the mouse's haptic feedback element (feedback control elements 132), thus providing vibrations (outputs for the human 134) to guide the user's further operation of the responsive device 112 or other responsive devices through the user interface device 102 or other user interface devices. While this example shows the feedback control elements 132 in the user interface device 102, in some cases, the feedback control elements 132 may be included in the responsive device 112, or in a combination of the user interface device 102 and the responsive device 112.

Figure 1B:
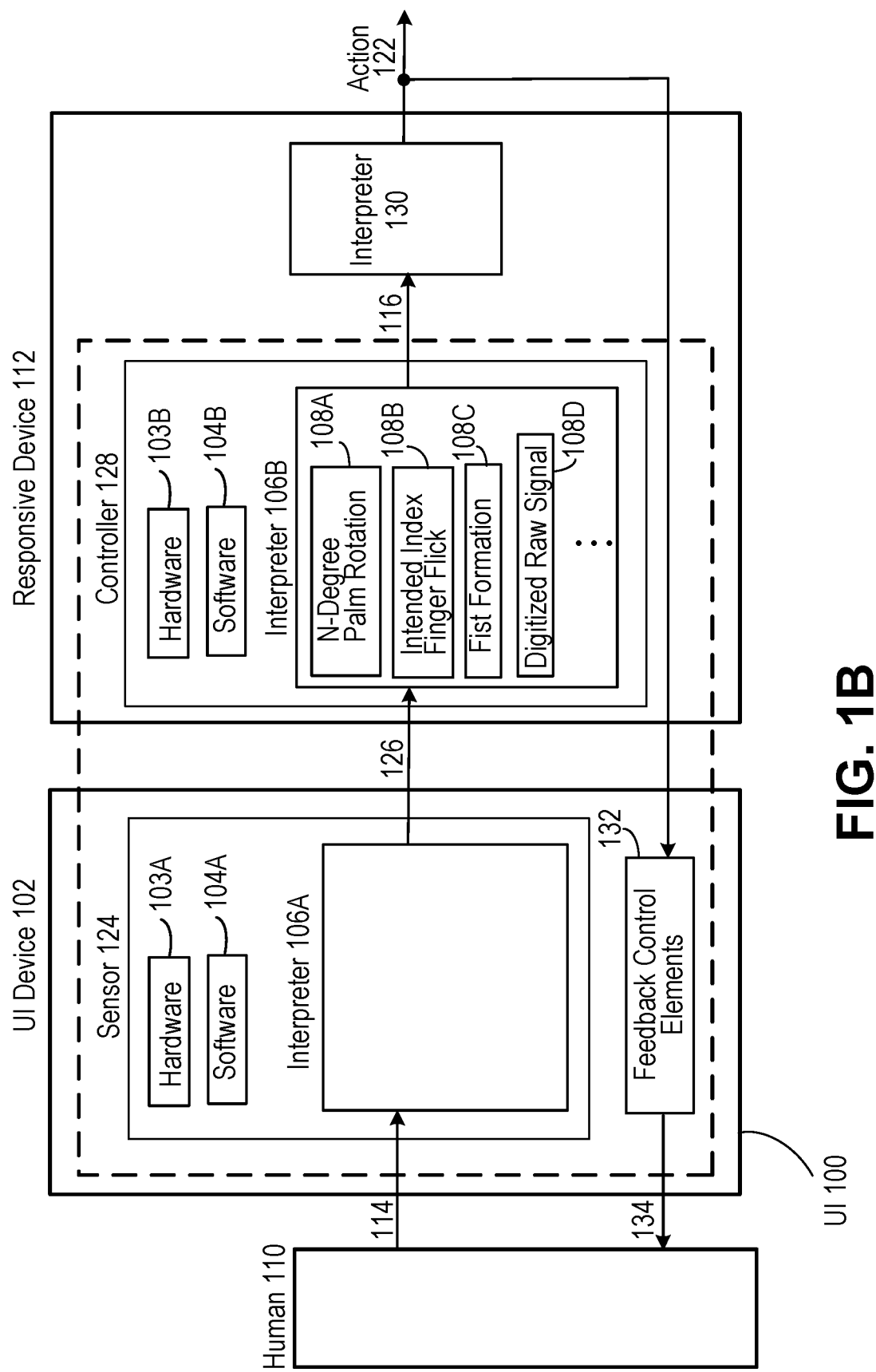

As mentioned previously, a user interface can be thought of as a conceptual technology that can take on various physical forms. FIG. 1B shows a configuration of a user interface 100, in which the user interface 100 is located (as indicated by the dashed lines) partially in a responsive device 112 and partially in a discrete user interface device 102. Similarly to the example shown in FIG. 1A, a human 110 generates biological inputs 114 that are detected by the sensor 124 and interpreted by the first interpreter 106A to generate output signals 126 representative of the biological inputs 114. However, in this configuration the user interface device 102 does not include the controller 128 with the second interpreter 106B. Rather, the controller 128 with the second interpreter 106B is located in the responsive device 112. The output signals 126 can be transmitted to the controller 128 in the responsive device 112 by sending electrical signals over a wired connection or by sending wirelessly transmitted radio frequency signals. The output signals 126 are received by the controller 128 within the responsive device 112, and the second interpreter 106B interprets the output signals 126 to generate an output 116 for the responsive device 112. Upon receiving the output 116 for the responsive device 112, the responsive device 112 interprets the output 116 using the interpreter 130 and performs the corresponding action 122. In some cases, in a closed loop user interface configuration, the action 122 may include sending a signal to feedback control elements 132 in order to generate outputs for the human 134.

FIGS. 1A and 1B show only example configurations and architectures of user interfaces and components and devices used to implement them. Configurations may include user interfaces having additional sensors, additional interpretation steps, multiple user interface devices, multiple responsive devices, and other combinations of components and devices.

Figure 2:
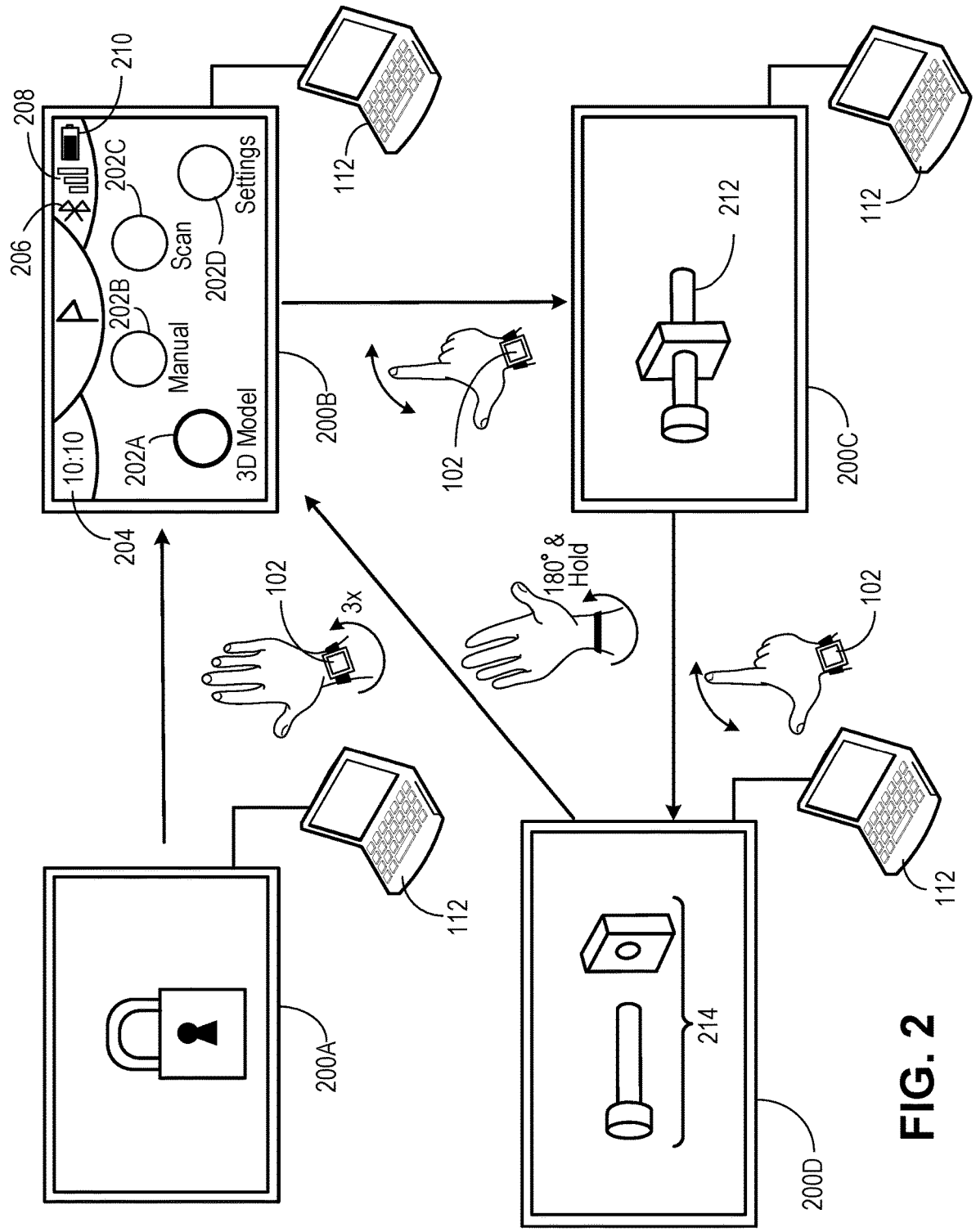

As shown in FIG. 2, a user interface 100 (for example, the user interface of FIG. 1A or FIG. 1B) can be used to operate, control, command, or otherwise operate any kind of responsive device 112 such as a computer or a mobile phone, to name two. In some cases, the responsive device 112 can perform actions that affect an on-screen display 200A-200D of the responsive device 112 at different moments. At a first moment, the on-screen display of the responsive device 112 may show a lock screen 200A. To unlock the screen, a user (human 110) wearing a wrist-worn user interface device 102 may rotate his palm 180 degrees (or some other angular amount within a range of 20 degrees to 360 degrees, for example) back and forth three times (or some other number of times such as a number of times between one and five) within a given time frame. The time frame may be between 0 and 3 seconds to correspond to the average time it takes a human to rotate his palm 180 degrees back and forth three times as quickly as possible. For example, the time frame may be between 0 and 1 seconds, 1 and 2 seconds, or 2 and 3 seconds, or other time frames. We use the term "rotate the palm" to refer, for example, to a motion in which a plane in which the palm lies is rotated about an axis that lies along the length of forearm. In some cases, rotation of the palm entails manipulation of the two bones of the forearm relative to the elbow.

Referring to the user interface configurations depicted in FIGS. 1A and 1B, the motion of the palm is a biological input 114 that is interpreted by an IMU sensor 124 included within the user interface device 102 to generate electrical signals 126 representative of the back and forth rotational motion. In the example being discussed, the controller 128 then classifies the electrical signals 126 as six consecutive "N-Degree Palm Rotation" gestures 108A, where N=180, −180, 180, −180, 180, and −180 (corresponding to three back and forth palm rotations). If the controller 128 determines that the three back and forth palm rotations occurred within the given time frame (e.g. 0-1 seconds, 1-2 seconds, or 2-3 seconds), the controller 128 generates an output 116 for the responsive device 112 commanding it to unlock (action 122) the lock screen 200A. In this example, the controller 128 combines (aggregates) six interpretations (i.e. "N-Degree Palm Rotation" gestures) of the interpreter 106B to generate a single output 116 for the responsive device 112. In general, the controller 128 can combine any number of similar or different interpretations 108A-C of the interpreter 106B into an action 122 depending on various contextual factors including, but not limited to, the timing of the interpretations, the type of responsive device 112, the status of the on-screen display 200A-D, the starting position or orientation of the hand, and combinations of them, among other things.

Upon unlocking (action 122) the lock screen 200A, the responsive device 112 shows a home menu 200B on the on-screen display. The home menu 200B includes selectable icons 202A-D representing applications that can be run by the responsive device 112. The home menu 200B includes a clock 204 and status indicators representing information about the responsive device 112 such as a Bluetooth connection 206, a network strength 208, and a battery life 210. In FIG. 2, the "3D Model" icon 202A currently has the focus for selection, as indicated by a thicker circular border. If a user (human 110) wishes to toggle through the icons, one by one, the user can rotate his palm clockwise once each time he wishes to toggle to the next icon. The motion (input 114) is interpreted to generate electrical signals or data 126, and the electrical signals or data 126 are classified as an "N-Degree Palm Rotation" gesture 108A. However, because the "N-Degree Palm Rotation" gesture 108A is identified while the user is working on the home screen 200B instead of on the lock screen 200A (in other words, the context is different), the output 116 generated for the responsive device 112 is different. Unlike while the user is working on the lock screen 200A, if the interpreter 106B interprets the electrical signals 126 as an "N-Degree Palm Rotation", the controller 128 does not wait to identify if three back and forth palm rotations are performed. In this case, if the interpreter 106B interprets the electrical signals 126 as an "N-Degree Palm Rotation", if N is greater than a pre-specified threshold amount in the clockwise direction (e.g., 10-15 degrees, or another pre-specified threshold amount in the range of 2 degrees to 30 degrees), the controller 128 immediately outputs a command to the responsive device 112 to scroll to the next icon in the order of "3D Model", "Manual", "Scan", and "Settings" (action 122). Similarly, the user (human 110) can rotate his palm counterclockwise (in accordance with the same or a different threshold amount) to toggle the icons 202A-D in a counterclockwise manner.

In some cases, if many icons are present on the on-screen display 200B, it can be uncomfortable for the user to rotate her palm 10-15 degrees every time she wants to move to the next icon, and if the rotation threshold is lowered too much, for example to 1-2 degrees, it could be challenging for a user to control. In some implementations, the user interface 100 can be configured so that the user can rotate her palm beyond the specified amount in the clockwise or counterclockwise direction (e.g. 10-15 degrees) once and hold her hand in that position to continue auto-scrolling in that direction. Likewise, to stop auto-scrolling, the user can rotate her palm once beyond the specified amount in the opposite direction.

A wide variety of other gestures can be expressed by a human user in the form of palm rotations. A variety of combinations of the number of rotations, the angular amounts of the rotations, and the durations of holding of the hand in a position can be used to represent a range of intentions and gestures. Various numbers of successive rotations in the same direction or in opposite directions and in any sequence could be used to express a variety of different intentions or gestures. A variety of different amounts of rotation could be used to express different intentions or gestures. And various combinations of amounts of rotations, numbers of successive rotations, and directions of rotations could be used to express different intentions or gestures. Rotations of the palm could be combined with other motions of one or more of the fingers or hand or both to express corresponding intentions or gestures. The hand motions could include pitch motions or yaw motions or combinations of them around the wrist relative to the forearm and such hand motions could be of various angular amounts, repetitions, directions, and combinations of them, in conjunction with palm rotations. Combinations of motions to express gestures or intentions could therefore range from simple to complex and could correspond to a wide variety of actions by the responsive devices. The angular orientation of the wrist and forearm can be used to differentiate between gestures. For example, pointing the hand and arm up is detectable by an IMU and can be mapped to an interface hierarchy command such as a home or menu command. Pointing the hand and arm diagonal upwards or downwards can similarly be used to navigate interfaces. Pointing down can be used to trigger a calibration state for the IMU for purposes of hand spatial tracking or resetting a user experience. In some cases, palm rotations can be combined with other gestures, such as flicking an index finger up, to correspond to a single action by the responsive device.

Referring again to FIG. 2, once an icon, say the "3D Model" icon 202A, has been toggled, to cause the responsive device to run the corresponding application (for example, the 3D modeling application) (action 122), the user (human 110) may flick his index finger up. An index finger flick up may comprise any rapid extension of the index finger, for example, beyond its anatomical resting position or beyond some other previously held position. For example, an index finger flick up may comprise the tip of the index finger moving within a range of 0-5 cm within a time frame of 0-500 ms. Other ranges of movement and time frames also could be considered finger flicks up.

Extensions and contractions of the index finger, as well as movements of any other body part, can themselves comprise extensions and contractions of various muscles. In some cases, remaining motionless also comprises the contraction of various muscles (i.e. in an isometric manner). We use the term "contraction" in the context of muscles broadly, to include for example, any activation of tension-generating sites in muscle fibers. We use the term "extension" in the context of muscles broadly, to include for example, any relaxation of tension-generating sites in muscle fibers or lengthening of the muscles.

In this example, the user interface device 102 on the user's wrist detects nerve or other tissue electrical signals (inputs 114), an electroneurography (e.g., nerve or other tissue electrical signal) sensor 124 generates corresponding electrical signals 126, an interpreter 106B classifies the electrical signals 126 as an "Intended Index Finger Flick Up" gesture 108B, the controller 128 sends a corresponding output command 116 for the responsive device 112 to open the 3D modelling application (action 122), and the responsive device 112 acts accordingly, for example, by launching the application whose icon has the focus.

Although in this example, we are referring to a rapid motion of a single finger as a gesture to trigger an action, rapid motions of other individual fingers (e.g., another finger or thumb) or combinations of two or more fingers could also be used as corresponding gestures. The speeds of motion and the extent of motion and combinations of them could be used to define different gestures. Combinations of motions of particular fingers or combinations of fingers with speeds of motion and extensive motion could provide additional defined gestures.

A user does not need to physically perform a gesture (for example cause an actual flicking motion of her index finger) in order to generate input that can be correctly classified as if it were a physical gesture by the user interface 100. Because nerve or other tissue electrical signals can be detected, interpreted, and acted on, irrespective of muscle contraction or extension, the intention of a user (for example, to effect a gesture such as the flick of an index finger) can be captured by the nerve or other tissue electrical signals, even in cases where the user is unable to contract or extend the muscles necessary to perform a gesture due to conditions such as Amyotrophic Lateral Sclerosis (ALS), stroke, or amputation.

Upon invoking the "3D Model" icon 202A in response to a correct interpretation of a user's index finger flick up as indicating a gesture to launch the application, the responsive device 112 shows a 3D workspace screen 200C on the on-screen display. In some cases, on this screen, rotations of the palm (inputs 114) can be interpreted to generate commands (outputs 116) to the responsive device 112 to rotate (or otherwise reorient) a presented assembly 212 in 3D space (action 122). In other words, gestures (palm rotation) similar to the ones described with respect to screen 200B, can be interpreted (based on the context of the rotation occurring with respect to a different screen display) as intending a different action by the responsive device, in this case rotation of a presented assembly. In addition, while the application is presenting the display 200C, nerve or other tissue electrical signals corresponding to an index finger flick up (inputs 114) can be interpreted (contextually) to generate a command (output 116) to the responsive device 112 to present an exploded view of the same assembly 214 as shown on screen 200D.

At any time, a user (human 110) can return to the home screen 200B by rotating her palm 180 degrees, for example, so that it is facing upward and by holding her palm in that position for a certain amount of time, for example, within a range of 1-3 seconds (or other ranges). By serving as a shortcut to the home screen 200B, this gesture allows for quickly switching between applications being run on the responsive device 112 and for easily navigating the menu hierarchy of the responsive device 112.

As shown in FIG. 2, a user interface can be used to control a responsive device based on a sequence of gestures or a combination of gestures that can be as simple or as complex as necessary to enable a full, rich, robust, or deep control of one or more (including every) feature, function, or capability of any kind of recognition device. In some respects, the library of gestures, sequences of gestures, and combinations of gestures can not only be sufficient to control every aspect of a recognition device, but in some circumstances the individual gestures, sequences of gestures, and combinations of gestures can be simpler, easier, quicker, and more robust in their control of the recognition device than can be provided by typical user interfaces.

The gestures can be mapped as shortcuts, used to trigger macros, or mapped to hotkeys of a responsive device in a universally accessible or a context-specific way. For example, an index finger flick up can be used to take a picture when the responsive device is in camera mode. The same gesture can be used to emulate a computer click when the responsive device is in a desktop navigation mode. Lifting a finger and holding for 1-5 seconds can be used as a universal gesture to lock the device from further commands except the unlock command which could be executed with the same gesture.

The example user interface for operating a responsive device, as described in relation to FIG. 2, could apply to the launching and running by the responsive device of a wide variety of applications in addition to, or instead of, the "3D Model", "Manual", "Scan" and "Settings" applications.

As mentioned above, additional gestures, both intentional and unintentional, may be performed to operate a responsive device 112, and the controller 128 can be configured to generate different outputs 116 in response to the same interpretations. For example, while "N-Degree Palm Rotation" and "Intended Index Finger Flick Up" gestures have been described, other finger, hand, or other body gestures may be interpreted. In particular, for user interfaces, it can be useful to use gestures that are performed infrequently by a user when he is not operating the responsive device 112 in order to avoid generating unintended actions of the responsive device 112. Supplemental or alternative gestures may include flicking an index finger down, forming a fist, remaining motionless (e.g. a pause or a hold), and abducting or adducting the fingers, or combinations of those.

Figure 13:
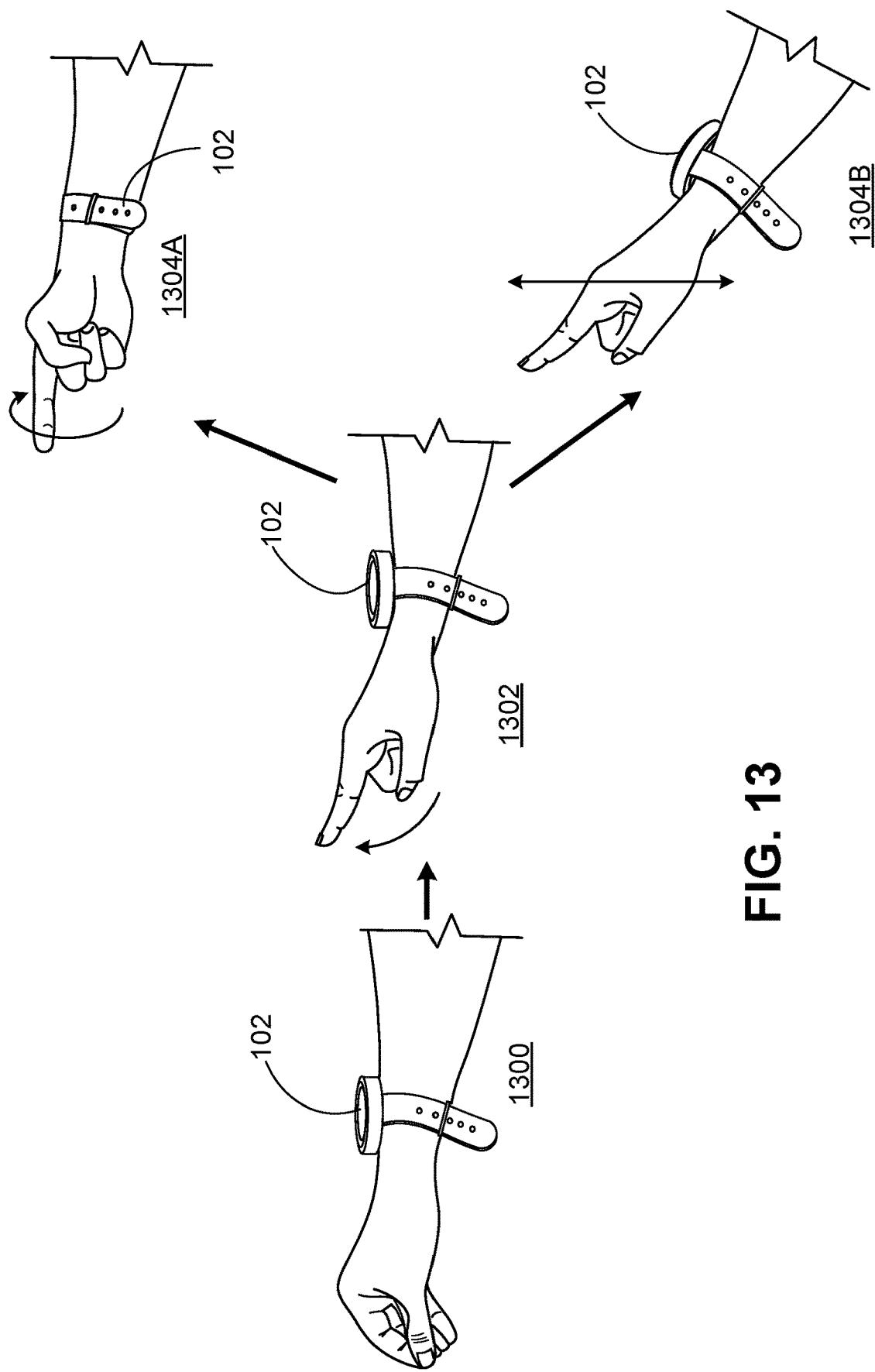

As illustrated in FIG. 13, in one supplemental gesture, the user starts with the hand in a resting position 1300, subsequently lifts his index finger up 1302, and rotates his palm 1304A within a time period of 0-3 seconds. While a clockwise rotation is shown, the rotation of the palm may also be in a counterclockwise direction.

Also illustrated in FIG. 13, in one supplemental gesture, the user starts with the hand in a resting position 1300, subsequently lifts his index finger up 1302, and raises his hand to point diagonally up 1304B within a time period of 0-3 seconds. While the user is shown to raise his hand to point diagonally up, in some cases, the supplemental gesture may comprise the user lowering his hand to point diagonally down. Raising or lowering the hand to point diagonally up or down can be performed, for example, by bending an arm at the elbow.

In some cases, a user interface device 102 can receive input signals (e.g. nerve or other tissue electrical signals or IMU signals) corresponding to one or both of these gestures and control a corresponding action of a responsive device 112 in accordance with the user interfaces 100 of FIGS. 1A and 1B. In some cases, the corresponding action of the responsive device 112 may depend on contextual factors such as the starting position or orientation of the hand and arm. For example, if one of the supplemental gestures described is performed with the hand and arm starting in a substantially horizontal orientation (as shown in resting position 1300), one corresponding action may be performed. However, if the same supplemental gesture is performed with the hand and arm starting in a substantially vertical orientation, a different corresponding action may be performed.

In addition to the benefits of providing inputs to a user interface already described in relation to FIG. 2, interpreting nerve or other tissue electrical signals occurring at, for example, the wrist (that is, "upstream") as corresponding to muscle contraction, extension, or both that the nerve or other tissue electrical signals will cause has other benefits. One of the benefit is in reducing the amount of time required for the user interface to determine the occurrence of a muscle contraction, extension, or both compared to user interfaces that require a user interface device, such as a mouse, a game controller, or another peripheral device, to be physically actuated by muscle contractions, muscle extensions, or both of the user. By detecting nerve or other tissue electrical signals, it is possible to interpret or register a user's intention to perform an action (e.g., make a gesture) 20-150 ms before a physical click on a mouse or game controller would be registered. This is especially important in applications such as e-sports or games or other applications, where users may perform up to 300 computer actions per minute (APM).

A common performance measurement for e-sports or performance sports in general is reaction time. Reaction time corresponds to the amount of time the brain takes to process a stimulus and execute a command to a part of the body to physically react such as by clicking a mouse. Typical reaction time can be 100 ms-400 ms. The amount of time saved in the interpretation of the user's intention can be significant with respect to the amount of time to perform the intended action of the responsive device to be controlled. In some examples, a user interface device that senses nerve or other tissue electrical signals can be placed on the anterior side of the wrist instead of the posterior side of the wrist to achieve improved detection of an intention to perform an index finger flick or a mouse click, for example. In some examples, the user interface device may be worn on the forearm for increased comfort. In some examples, to reduce false positives, a touch sensor may be included on a mouse or game controller so that the user interface device sends an output to the responsive device to perform a mouse click only when a user's hand is placed on the mouse or game controller.

In addition to the benefits of providing inputs to a user interface already described in relation to FIG. 2, interpreting nerve or other tissue electrical signals occurring at, for example, the wrist (that is, "upstream" or proximal) as corresponding to muscle flexion or extension, that the nerve or other tissue electrical signals will cause, may have other benefits. One of the benefits is a reduction in time required for the user interface to interpret (e.g., predict) the occurrence of a muscle flexion or extension, compared to interfaces that require a user interface device, such as a mouse, a game controller, or another peripheral device (e.g., a physical peripheral device), to be physically actuated by muscle flexion or extension (or any muscle contractions) of the user. By detecting nerve or other tissue electrical signals "upstream", it is possible to interpret or register a user's intention to perform an action (e.g., make a gesture) 20-150 ms before a corresponding physical click on a mouse or game controller would be registered. On average, the prediction of the physical click could precede the actual click by, for example, about 30 milliseconds. This is especially important in applications such as e-sports or games or other applications, where users may perform up to 600 computer actions per minute (APM).

A common performance measurement for e-sports or performance sports in general is reaction time. Reaction time corresponds to the period required for brain processing of a stimulus and the execution of a decision (command) to move a part of the body (e.g., limb or finger) in order to complete a physical action, such as clicking a mouse device. Typical reaction time can be 100 ms-400 ms. The reduction in overall reaction time, through a predictive interpretation method, can significantly impact the intended functioning of the responsive device to be controlled, in a time sensitive task.

In the field of competitive video games, especially, the outcome of a match can depend upon millisecond differences in reaction time. For example, in a first-person shooter (FPS) game, the winner of a one-on-one engagement is the player who is able to shoot first and hit the enemy target. In some FPS games, a user whose input is detected a mere 10 milliseconds after a competitor's input might result in a loss. In real time strategy games (RTS) like StarCraft 2, the victor of a match tends to be the player with the most actions per minute (APM). A player with superior reaction time, with lower-latency input, is likely to have a higher APM, and therefore win.

In some examples, a user interface device that senses nerve or other tissue electrical signals can be placed on the anterior side of the wrist instead of the posterior side of the wrist to achieve improved detection of an intention to perform an index finger flick or a mouse click, for example. In some examples, the user interface device may be worn on the forearm for increased comfort. In some examples, to reduce false positives, a touch sensor may be included on a mouse or game controller so that the user interface device sends an output to the responsive device to perform a mouse click only when a user's hand is placed on the mouse or game controller.

Figure 14:
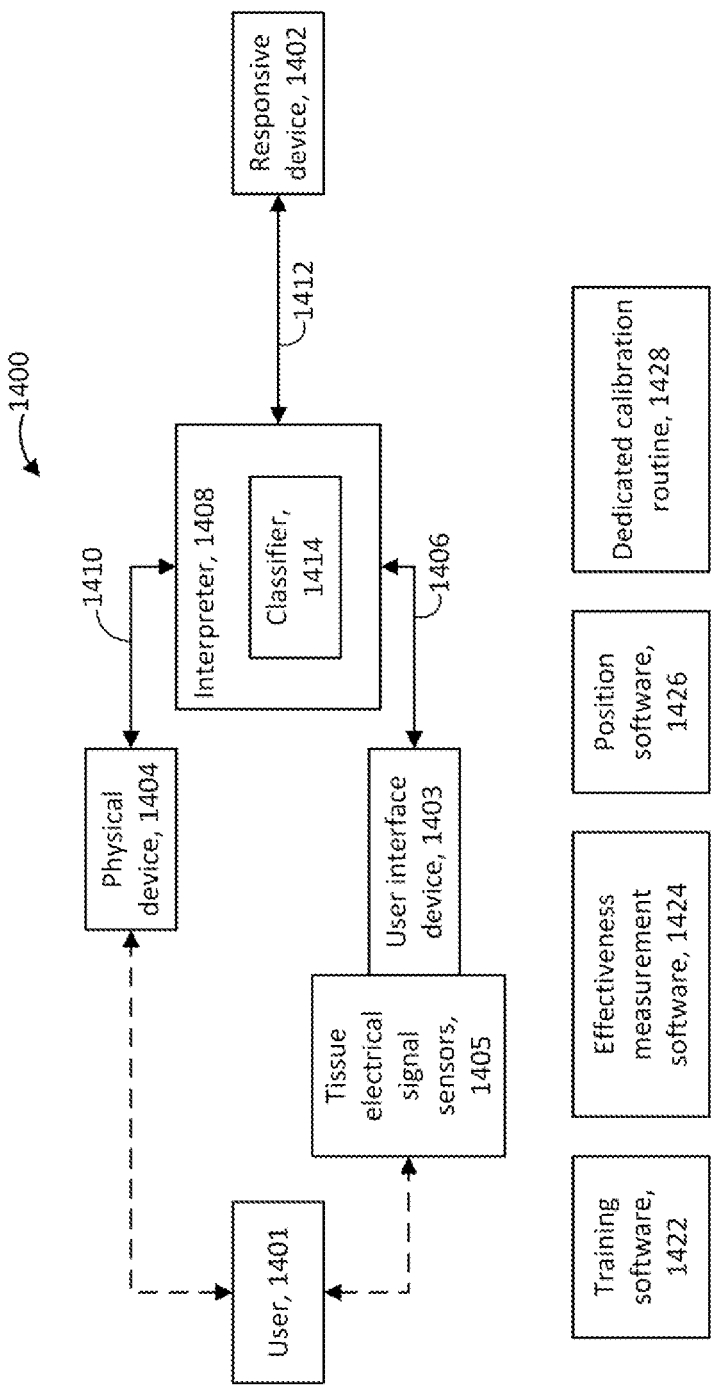

As shown in FIG. 14, in some implementations of the user interface system 1400, a player of a game (e.g., a game console, electronic game, or game software running on a general-purpose device) or generally a user 1401 of a responsive device 1402 typically uses one or more fingers or a hand to manipulate physical features of a mouse (or trackball, touchpad, game controller, or other similar device) or another physical device 1404 to indicate an action to the game or other application. We sometimes use the word "game" broadly to refer to a game or any other application. We sometimes use the word "mouse" to refer broadly to, for example, a traditional mouse or to any other physical user interface device.

In addition to the physical device 1404, a user interface device 1403 can be worn at the same time on the user's wrist or another part of the user's arm associated with the hand or fingers that are used to manipulate the physical device. The user interface device can include tissue electrical (e.g., biopotential) signal sensors 1405 as described earlier. In some cases, the signal sensors can face the anterior side of the wrist.

Signals 1406 from the user interface device and signals 1410 from the physical device can be transmitted to an interpreter 1408 wirelessly (for example on a Bluetooth low energy channel) or by wire or a combination of the two.

In some implementations, the signals 1410 take the form of a stream of binary signals (e.g., on and off) representing, for example, the clicks of a mouse. In some cases, the signals 1410 can take the form of a stream of non-binary signals (e.g., representing signal levels within a range). The signals 1410 therefore represent, for example, the states of physical switches or physical variable controls belonging to the physical device. The signals 1410 can be sampled frequently (say, for example, at a rate of 10 Hz). And the physical device or the interpreter can timestamp each sample and store it for later analysis and use.

Similarly, in some cases, the signals 1406 take the form of a stream of binary signals or analog signals sampled at a similar rate. The samples represent one or more tissue electrical signals detected at the skin of the user. The stream of signals 1406 can include raw signals, processed signals, or interpretations of the raw signals for use by the interpreter. The physical device or the interpreter can timestamp each sample and store it for later analysis and use. Although FIG. 14 shows the interpreter as a separate device, as discussed earlier, the interpreter functions can be performed either in a separate device or the physical device in the user interface device, in the responsive device, or in combinations of any of them.

One function of the interpreter 1408 is to provide signals 1412 to the responsive device 1402 in a format and in substance corresponding to commands or information expected by the responsive device concerning the interaction between the user and the responsive device. For example, if the responsive device is a general-purpose computer running a game, an expected signal from the interpreter could be one indicating that the user has clicked the mouse to indicate an action that should be taken on the game.

Traditionally, in a user interface system that includes a physical device, and does not include a user interface device 1403, the interpreter provides the signals 1412 directly to the responsive device based on the signals 1410 received from the physical device. For example, when a user clicks a mouse, the interpreter sends a mouse event to the operating system of the responsive device.

In the user interface system 1400 shown in FIG. 14, the interpreter may or may not simply pass the mouse click events through from the physical device to the responsive device. By applying a classifier to the tissue electrical signals, the interpreter may be able to determine that a muscle contraction is imminent, to predict that a mouse click is about to occur, and to make that prediction some small amount of time, for example, 30 ms more or less ahead of the time when the signal from the physical device indicates that the mouse click has actually occurred. In such cases, the interpreter can send a mouse click event to the operating system of the responsive device earlier than it would otherwise have done so. As a result, the user's interaction with an experience in playing the game or other application is enhanced significantly.

In some implementations, the interpreter can use the earlier to occur of the tissue electrical signals and the mouse signals to infer the occurrence of a mouse click and provide the mouse click event to the responsive device based on the earlier to occur. In effect, the interpretation of the tissue electrical signals can enable accurate predictions of the mouse clicks earlier than the actual mouse clicks, making the game player a better player and enhancing the game experience.

All tissue electrical signals, mouse clicks, and their corresponding timestamps can be stored in the physical device, the user interface device, the interpreter, or the responsive device, or combinations of them, for later analysis and use.

In some implementations, the determination that a mouse click is about to occur can be made by a classifier 1414 (or other machine learning or artificial intelligence process) running as part of the interpreter, the physical device, the user interface device, the responsive device, or a combination of them. When the classifier is operating in the user interface device, for example, the classifier, parameters for its operation, and its configuration can be downloaded wirelessly or through a wired USB connection, for example, from the interpreter and 10 be updated as improvements are made to the classifier or additional training data becomes available. Other settings for the interface device 1403 can also be downloaded and stored in firmware on the interface device. The classifier, parameters, configuration, training data, and other settings can be updated on-the-fly.

In some cases, the user interface device 1403 can include additional mechanical and electronic features to improve the performance of the user interface system 1400. For example, mechanical features can be provided to help to assure a predetermined location and orientation of the user interface device on the user so that, for example, a set of electrodes reliably face the anterior side of the wrist with respect to the radial compartment of the anterior wrist. In some instances, the electrodes can provide two channels of signals from the wrist, the first channel from the radial compartment and the second channel from the target flexor digitorum profundus to enhance the robustness of the information available for classification.

In some examples, a second sensor or set of sensors could be included on the user interface device positioned and oriented to face the posterior wrist on the radial side to detect and classify tissue electrical signals associated with extension movements of one or more fingers. The signals from the second sensors can be used to enhance the quality of the classification of mouse events and to enable classification of other occurrences related to the mouse.

In some cases, the user interface device can be implemented as implantable sensors in the user's wrist or tattoo-based or sticker-based flex circuits that would conform to the user's skin, or combinations of them.

In some implementations, other types of sensors can be included as part of the user interface device, the physical device, or other components of the user interface system 1400. For example, capacitive sensors could be used to confirm when the user's hand is touching or resting on the mouse. In some embodiments, the interpreter would not predict a mouse click when the user's hand is not touching or resting on the mouse. In some cases, the sensors could include proximity sensors or photo-resistors. Such other sensors and components can be held on the body of the user in the vicinity of the user interface device or off the body. Signals from the sensors can provide additional information for use in classification of events or actions intended by a user.

In some implementations, the user interface device can be held on the forearm above the wrist including near the wrist, near the elbow, or in between. The farther the user interface device is held above the wrist, the greater the possible time difference between the tissue electrical signals and the corresponding physical mouse click, potentially enhancing the beneficial effects mentioned earlier.

Although the user interface device can, in some implementations, be a distinct "standalone" device, in some cases, some or all of the features and functions of the user interface device can be integrated in another device, such as a bracelet, a watch, or a mouse, or combinations of them. In some cases, functions and features of the user interface device can be incorporated directly into the physical mouse either in its original construction or as an add-on, and the two can be coupled by wired or wireless connections.

In some instances, sensors such as proximity sensors can be integrated into a physical mouse to detect whether contact is being made by a user with the device. The signals from the integrated sensors can be provided to the interpreter for use in confirming that tissue electrical signals classified as mouse clicks, for example, are likely accurate because the user is actually touching the mouse.

In some implementations, a physical mouse click may not be necessary in order for the interpreter to predict a mouse click accurately. In other words the user may be touching the mouse and may send signals from her brain associated with an intent to click the mouse, but the signals need not result in a physical mouse click for the interpreter to correctly interpret that a mouse click is intended.

In some cases, the user interface device and a physical mouse could be physically or electrically (or both) interconnected and could share data connections to the interpreter, which can reduce the need for multiple cables and improve transmission speeds.

In order to optimize the accuracy of the prediction of a user physical mouse click by the techniques described above, it can be desirable to calibrate and retrain the classifier using the occurrences and timing of the physical mouse clicks and the signals from the user interface device. By acquiring a stream of data about tissue electrical signals and labeling segments of the data as corresponding to physical mouse clicks, training data can be generated that can be used to update the training of the classifier. This calibration updating process can be executed continuously as the user interface device and the physical mouse are being used in a live gaming context.

In some cases, calibration and training of the classifier can be done by training software 1422 dedicated to that function. The training software could include a game (such as electronic target practice or skeet shooting) that involves frequent physical mouse clicking. A stream of data taken from the user interface device while a particular user plays the game then can be labeled by data representing physical mouse clicks. The labeled data can then be used to train the classifier for use by that user.

The data streams received by and processed by the interpreter will depend on the particular type of physical mouse being used, the particular behavior of the individual physical mouse, the physical and electrical characteristics of the user interface device, its location on the user, the style of mouse click and use by particular user, the particular game being played, and a wide variety of other factors. It is useful to calibrate and train the classifier to take account of such factors. Effective training and retraining of the classifier can optimize its effectiveness in correctly predicting the existence and timing of physical mouse clicks.

In some instances, effectiveness measurement software 1424 can be executed on data streams derived from operation of the user interface device and a particular physical mouse by the user. Metrics can be devised to measure the effectiveness of the use of the user interface device in providing accurate predictions of the physical mouse clicks. The metrics can be reported to the user along with high level simple interpretations such as "This device may not provide any benefit in accelerating your game play." In some examples, users may not benefit because of their physiology, the placement of the user interface device, their preference of mouse type, or other factors. As a result of such factors, the physical mouse clicks may be delivered sooner than the tissue electrical signals can be classified.

In some implementations, position software 1426 determines the position and orientation of the user's hand relative to the physical mouse, which enhances the ability of the classifier to reduce false positive predictions and false negative predictions of the existence of physical mouse clicks. The position software can use signals from sensors, cameras, gyroscopes, and accelerometers, and combinations of them, on the user interface device, the physical device, or the recognition device, or combinations of them, for this purpose.

The level of mouse activity can also be a relevant factor in the determination of position and orientation. Among the sensors that could be used are force sensitive resistors, IMUs, proximity sensors, capacitive sensors, and photoresistors, and combinations of them. The hand position and orientation can be determined continuously during use of the user interface device and mouse, and the results used as inputs to the classifier, for example. In some cases, the information can be used to provide feedback to coach the user on more effective hand positions and orientations.

In some cases, the user interface device, its interaction with the physical mouse, and the interpreter can be configured by or for a given user to customize their use and operation for that user and to affect how they respond to the user during a gaming session. For example, the sensitivity of the classifier to the actions of the user can be set to predict the occurrence of physical mouse clicks at a selected degree of "hardness" of the mouse click, such as a hard click or a soft click, depending on the tissue electrical signals captured. The classifier could also be configured to recognize different types of motion of fingers of the user as representing physical mouse clicks or other physical device actions, such as contractions of muscles (or extensions) of the thumb, the middle finger, the index finger, or the pinky finger, or combinations of them. In some applications, these motions are different from or unrelated to physical mouse clicks. For example, the interpreter can be configured to predict a physical mouse click when the user extends her index finger without regard to whether the extension achieves a physical mouse click and without regard to whether a physical mouse is present in the context.

In some examples, the classifier can not only predict the existence and timing of physical mouse clicks, but also determine how hard the user is pushing (the pressure) on the physical mouse button. The ability to track the degree of pressure on the mouse button can provide useful additional information about intended actions. Such information can be used to provide a richer, more complex, and more subtle range and types of interactions between the user and the game than is possible with simple binary mouse clicks.

In some cases, the inclusion of one or more IMUs in the user interface device, the physical device, or other components of the user interface system can be used to track subtle wrist rotations and other motions on the physical device. Such subtle motions can be mapped to gestures relevant to a context of a game. A user of a game typically is not only performing mouse clicks but also voluntarily or involuntarily manipulating her arm, wrist, or fingers in ways to indicate or imply actions that are relevant to the game. Such manipulations can be interpreted by the classifier as, for example, a "lean" gesture or a "strafe" gesture.

IMU data also can be used to silence or otherwise affect a mouse click or other physical action on a physical device. In some cases, the IMU signals may be combined with activation signals to enable the classifier to predict a mouse click. In addition, combinations of data from the IMU and other sources can be used by the classifier to determine a variety of different mouse actions (left click, right click, middle click, thumb buttons, and mouse cursor motion, among other things). A gaming mouse implemented in this way could have up to 20 programmable keys.

In some cases, the user interface device or the physical mouse or both can provide feedback to a user with respect to mouse clicks. For example, the feedback could confirm physical mouse clicks or the duration of physical mouse clicks or both. The feedback can also confirm mouse down and mouse up events separately.

In some examples of the operation of the system, the following sequence of hardware and software interactions can occur.

Biopotential signals are collected at the anterior portion of the wrist and delivered to local circuitry on the user interface device. The signals can be processed at the user interface device or forwarded in their raw state to the interpreter or a combination of the two. The signals can be carried over Bluetooth low energy channel to the interpreter. In some cases, combinations and sequences of biopotential signals are classified on board the user interface device and the classifications (indicating, for example, a mouse click) are sent to the interpreter. In some instances, combinations and sequences of biopotential signals are classified in the interpreter.

The interpreter receives two streams of data with respect to mouse clicks. One stream is derived from the biopotential signals collected at the user interface device. The other stream is received from the physical mouse button switch. In each of the two streams of mouse click data, each of the mouse click events is time stamped. By analyzing the timestamps for the respective mouse click events in the two streams of data, the interpreter can match corresponding mouse click events in the two streams. Often, for example, the mouse click event in the user interface device will occur slightly ahead of (for example in a range around 30 ms) the mouse click event in the physical mouse click stream. Two corresponding mouse click events are paired to form a click-pair. The click-pair is analyzed by the interpreter to determine which mouse click event occurred first. The interpreter then posts the earlier-to-occur mouse click event of the click-pair to the event queue of the operating system where it is treated as a mouse click.

In addition, the time stamped streams of data are stored and used for analytical purposes. For example, the data can be used to calculate user performance metrics, can be used for training the classifier, and can be used for development and improvement of the system, among other things.

As discussed earlier, before the user interface device is ready for use, a user calibration can be performed to optimize the performance and reliability of the classifier as applied to a particular user. Various techniques can be used for calibration including the following. The system can be continuously calibrated dynamically based on currently collected data streams from the user interface device and the physical mouse. The system could be calibrated using a dedicated calibration routine 1428 run prior to the actual use of the user interface device. The dedicated calibration routine could be specifically designed for that purpose. In some cases, a user can make adjustments and additions directly to suit her intentions.

In general, mouse click event data from the user interface device and from the physical mouse as well as calibration data, calibration performance, and quality metrics can be provided directly to the user in various forms. Among other things, this can help the user to improve her use of the system, including improving average speed benefit relative to standard physical mouse clicks.

Processing of streams of mouse click event data, developing and distributing classifier and other machine learning software, managing user profiles, and a variety of other functions and features can be provided either from a cloud-based server system or through a client-based system located with the user, or combinations of the two.

In some cases, multiple classifiers could be maintained and operated on the interpreter and the user could be given the opportunity to choose which classifier she wishes to have applied to her use of the user interface system. The user could also determine custom preferences, for example the threshold for the determination of whether a mouse click is a hair-trigger mouse click or a heavy-handed mouse click.

Although much of the discussion above has been focused on the use of the physical mouse, mouse clicks, and the attachment of the user interface device for sensing tissue electrical signals at the anterior side of the wrist, the techniques that are described can be applied to a wide variety of other devices in contexts. For example, they can be applied with respect to any physical device that can be physically manipulated by a user, for example, by one or more fingers or wrist of the user. The user interface device can sense tissue electrical signals at a variety of other places on the arm. Although gaming has been the focus of some of the examples discussed above, the techniques can be applied in a wide variety of contexts and applications, including industrial and commercial applications and in the control of a wide variety of productivity, design, and management applications.

Figure 3:
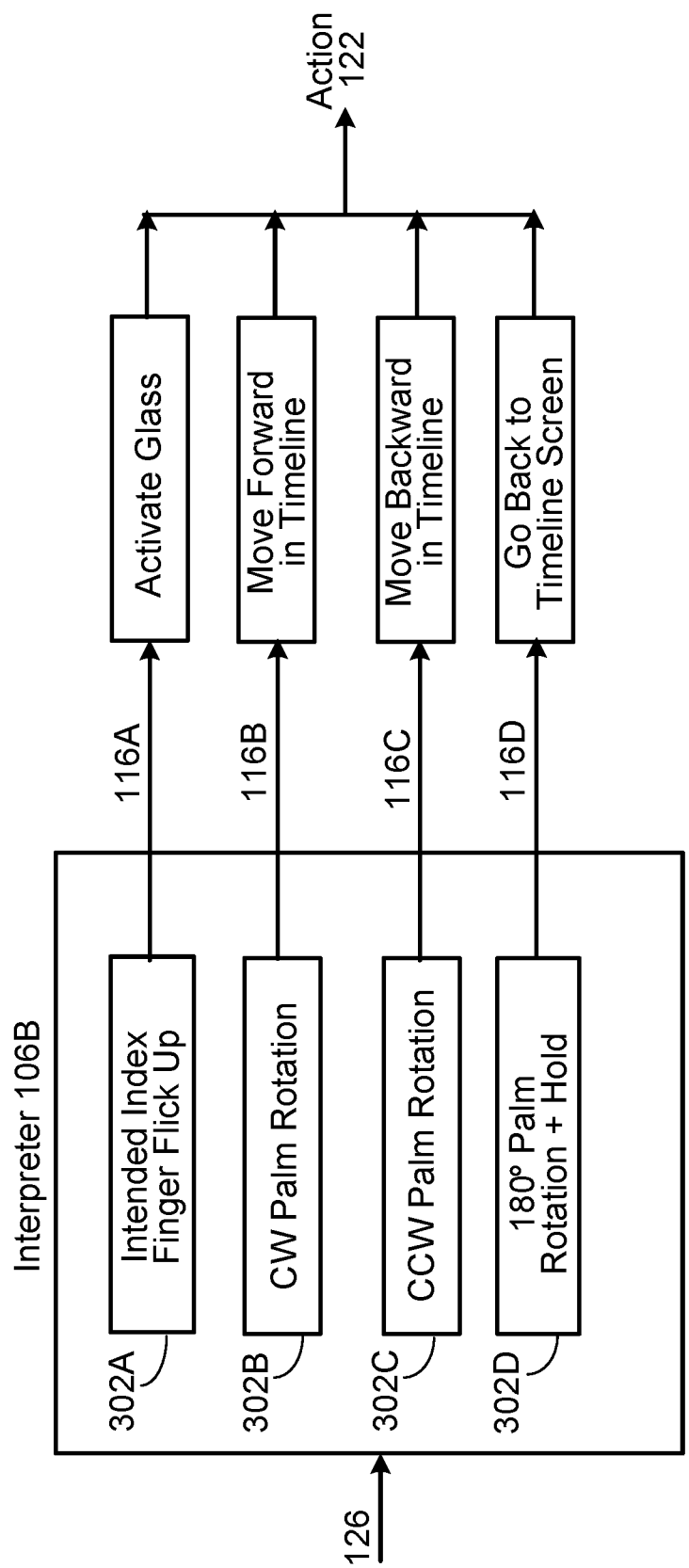

Referring to FIG. 3, a pair of smart glasses is another example of a responsive device that can be controlled, commanded, informed, or otherwise operated using a user interface, such as the user interfaces 100 of FIGS. 1A and 1B. In order to operate the smart glasses, the second interpreter 106B may include specialized interpretations 302A-D particularly suited to operation of smart glasses. As before, the second interpreter receives electrical signals or data 126 representative of inputs 114 from the human 110 and interprets the electrical signals or data 126 to generate outputs 116A-D for the smart glasses (responsive device 112). In this example, the outputs 116A-D for the smart glasses are commands to perform one or more actions 122. For example, if the second interpreter 106B classifies the electrical signals 126 as an "Intended Index Finger Flick Up" gesture 302A, an "Activate Glass" command 116A is generated, and the smart glasses perform the corresponding action 122. If the second interpreter 106B classifies the electrical signals 126 as a "Clockwise Palm Rotation" gesture 302B, a "Move Forward in Timeline" command 116B is generated, and the smart glasses perform the corresponding action 122. If the second interpreter 106B classifies the electrical signals 126 as a "Counter-clockwise Palm Rotation" gesture 302C, a "Move Backward in Timeline" command 116C is generated, and the smart glasses perform the corresponding action 122. If the second interpreter 106B classifies the electrical signals 126 as a "180 Degree Palm Rotation & Hold" gesture 302D, a "Go Back to Timeline Screen" command 116D is generated, and the smart glasses perform the corresponding action 122. Thus, the user (human 110) can provide input 114 to operate the smart glasses (responsive device 112) without moving his hands toward the smart glasses or touching the smart glasses directly. Compared to user interfaces that include a touchpad that is physically located on the smart glasses, the user interface described here has the advantages of improved ergonomics, energy efficiency, and time savings. Control of the responsive device can be rapid, simple, easy, and effective.

Figure 4:
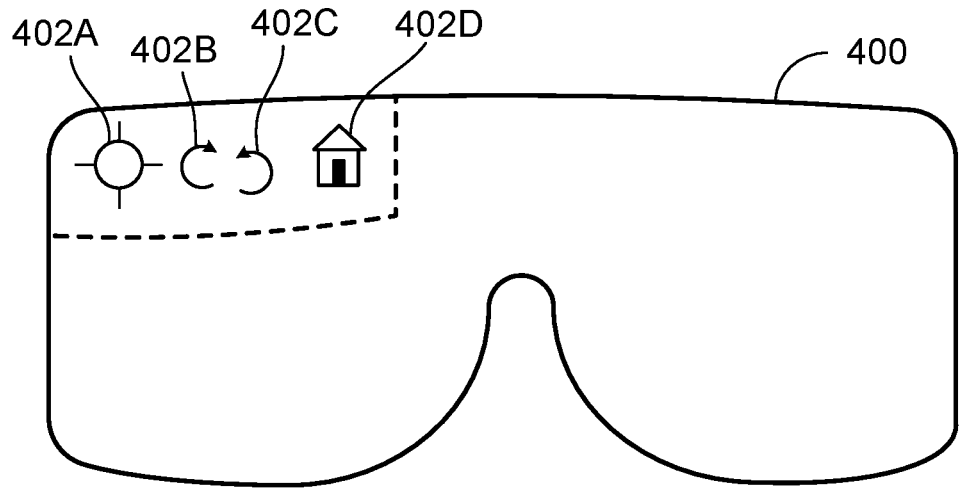

FIG. 4 shows an example on-screen display 400 of a pair of smart glasses (responsive device 112). The on-screen display 400 includes visual feedback icons 402A-D that indicate to a user that a particular output 116A-D for the smart glasses has been generated. For example, referring back to FIG. 3, if an "Activate Glass" command 116A is generated, visual feedback icon 402A may indicate this to the user (human 110) by changing color, flashing on and off, increasing in size, or giving any other visual indication. If a "Move Forward in Timeline" command 116B is generated, visual feedback icon 402B may indicate this to the user. If a "Move Backward in Timeline" command 116C is generated, visual feedback icon 402C may indicate this to the user. If a "Go Back to Timeline Screen" command 116D is generated, visual feedback icon 402D may indicate this to the user. While visual feedback icons are described here in the context of smart glasses, it is understood that these icons can be included on the on-screen display of any responsive device 112 to inform a user when a particular output has been generated. In some cases, audio or haptic indicators can be included in addition to, or instead of, the visual feedback icons described in relation to FIG. 4. For example, each of the commands 116A-D may be associated with a unique audio output that is produced by the responsive device 112 when the command is generated. In some examples, each of the commands 116A-D may be associated with a unique vibration pattern of a haptic feedback element included within the body of the responsive device 112.

Control of the wide variety of other features and functions of smart glasses or applications running on smart glasses can be achieved by one or more user interfaces that rely on nerve or other tissue electrical signals.

Figure 5:
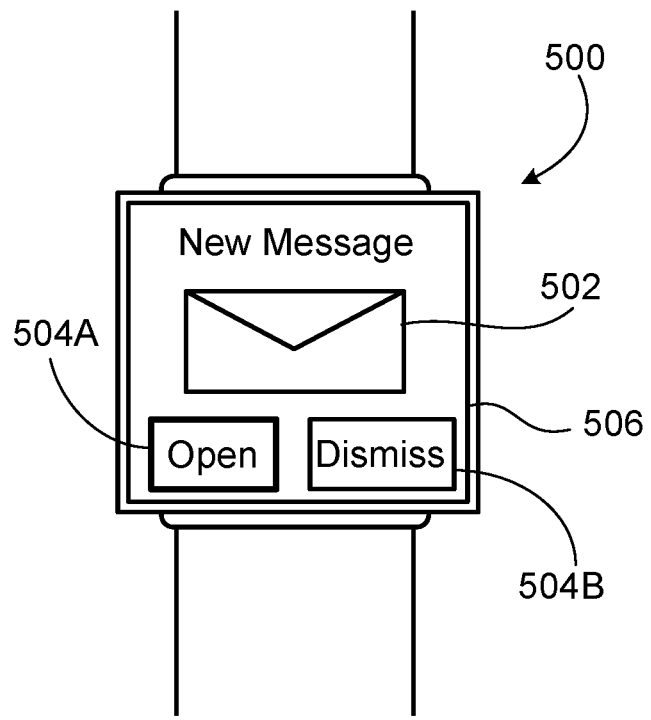

Referring to FIG. 5, a smartwatch 500 is an example of a responsive device 112 that can be controlled, commanded, informed, or otherwise operated by a user interface such as the user interfaces 100 of FIGS. 1A and 1B. Notification management and information accessibility are key features of smartwatch designs. A smartwatch 500 can pair with another wireless device, such as a smartphone, and pass information to the user using tactile, visual, auditory, or other sensory cues, or a combination of them. For example, as shown in FIG. 5, the on-screen display 506 of the smartwatch 500 shows a visual icon 502 indicating that a new message has been received. The on-screen display 506 also shows two selectable buttons 504A and 504B, giving the user the option to open the message or dismiss the notification. Currently, the "Open" button 504A is toggled as indicated by thickened borders.

Applying a user interface such as the user interfaces 100 of FIGS. 1A and 1B in this context, if a user (human 110) desires to open the message, he can flick his index finger up. The nerve or other tissue electrical signals from this motion (input 114) are interpreted by a first interpreter 106A located in a sensor 124 to generate electrical signals 126 representative of the detected nerve or other tissue electrical signals. The generated electrical signals 126 are then classified by a second interpreter 106B located in a controller 128 as an "Intended Index Finger Flick Up" gesture 108B, and an output 116 is generated to cause the smart watch (responsive device 112) to select the toggled "Open" button 504A (action 122). Alternatively, if the user desires to dismiss the notification, he can rotate his palm clockwise to toggle the "Dismiss" button 504B and then perform an index finger flick up to cause the smartwatch 500 to perform a selection action.

In addition to opening and dismissing notifications, a user interface such as the user interfaces 100 of FIGS. 1A and 1B can be extended to respond to notifications as well as navigate and operate the various menus and applications run by the smartwatch 500. Thus, the user (human 110) can provide input 114 to operate the smartwatch (responsive device 112) without using his opposite hand (the one not wearing the smartwatch) or touching the smartwatch screen 506 directly. Compared to user interfaces that require touch control, the user interface described here has the advantages of improved ergonomics, energy efficiency, and time savings, among other benefits.

Figure 10:
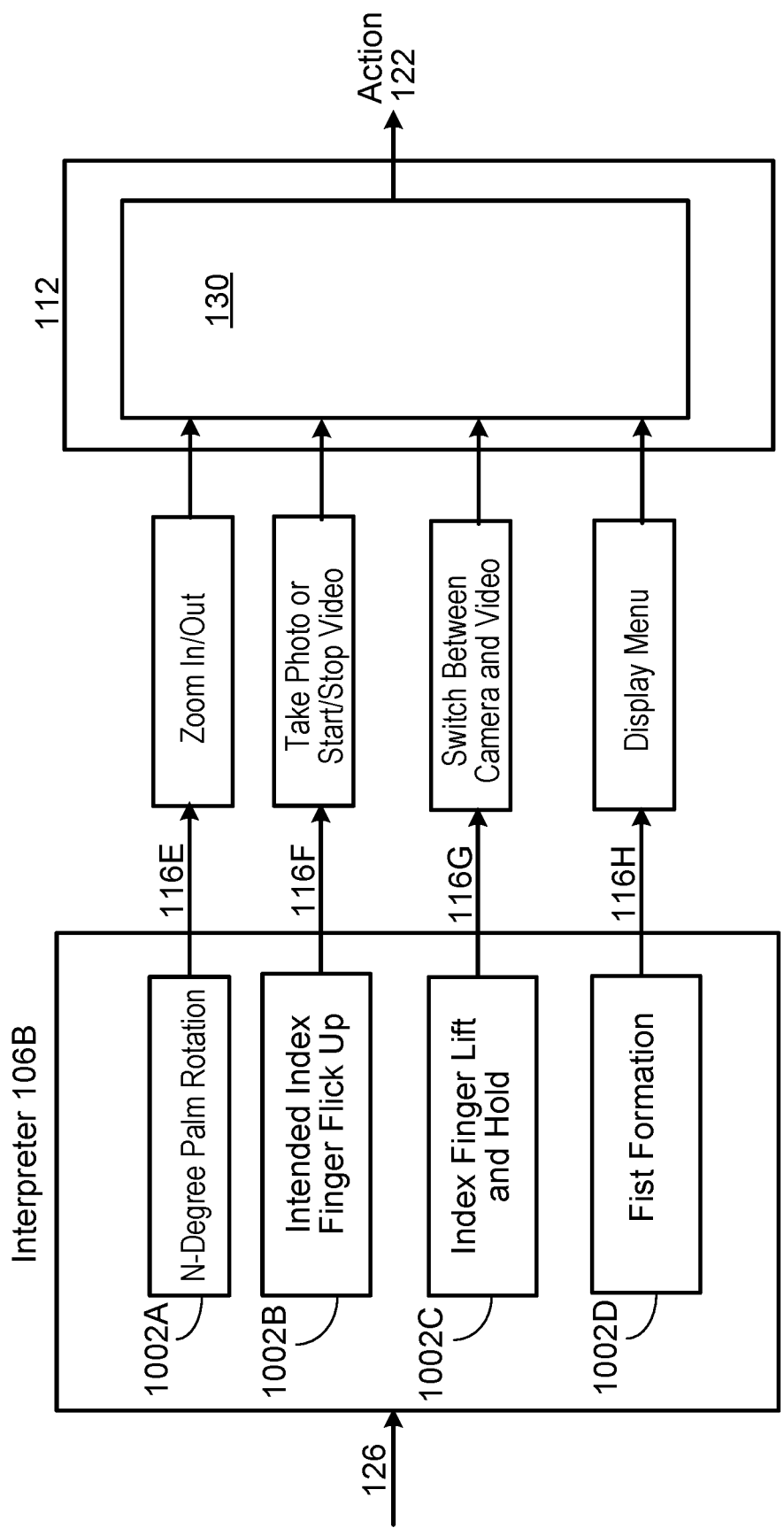
Figure 11:
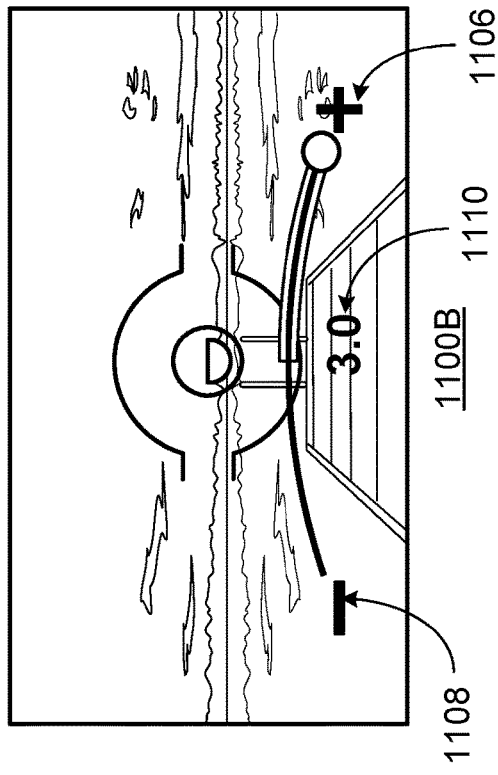
Figure 11:
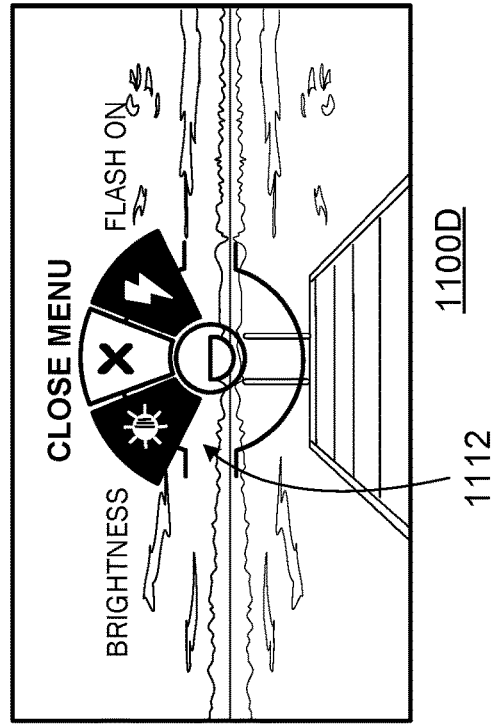
Figure 11:
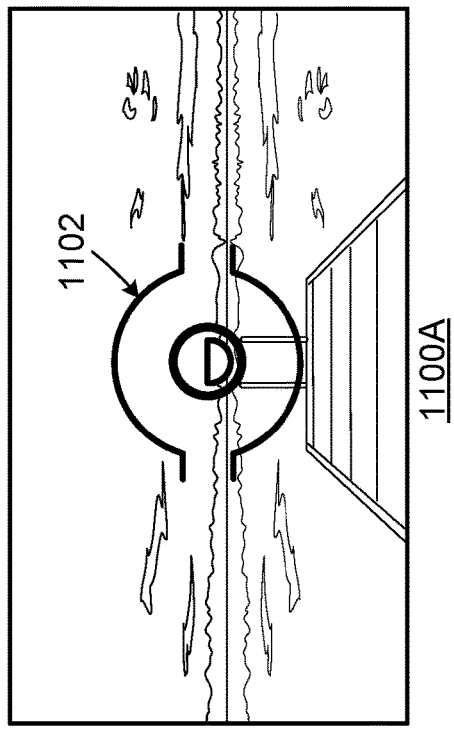
Figure 11:
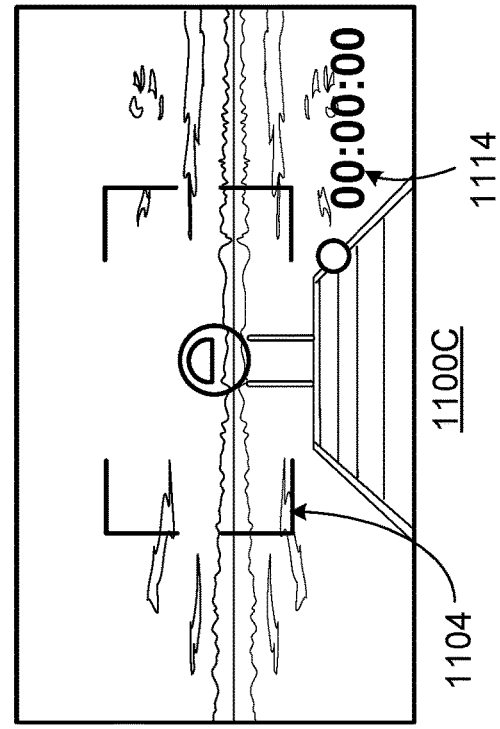
Figure 12:
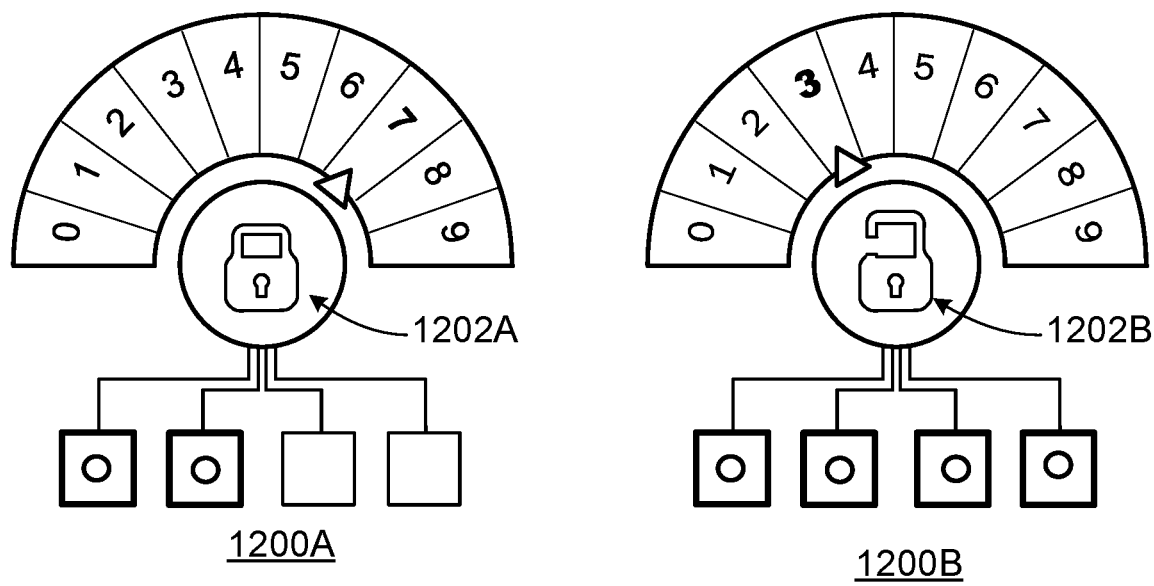

Referring to FIGS. 10 and 11, a camera is an example of a responsive device 112 that can be controlled, commanded, informed, or otherwise operated using a user interface such as the user interfaces 100 of FIGS. 1A and 1B. In some cases, the camera can be a standalone device such as a hand-held camera, a remote camera, or a security camera. In some cases, the camera can be included in or connected to a camera-compatible device such as a smart phone, a drone, a pair of smart glasses, or any other camera-compatible responsive device. While the examples that follow describe the generation of direct outputs for the camera, in some cases, outputs may be generated for an intermediary device such as a camera-compatible device that runs an application for controlling actions of the camera.

In order to operate the camera, the second interpreter 106B may include a specialized set of interpretations 1002A-D appropriate to the camera. The second interpreter 106B receives electrical signals 126 representative of inputs 114 from the human 110 and interprets the electrical signals 126 to generate outputs 116E-H for the camera (responsive device 112). In this example, the outputs 116E-H for the camera are commands to perform an action 122 when the camera is in an active state. The active state of the camera can be presented on an on-screen display, showing, for example, an active camera default screen 1100A (shown in FIG. 11). In some cases, the on-screen display can be a screen on or connected to a standalone camera or a camera-compatible device. For example, if the second interpreter 106B classifies the electrical signals 126 as an "N-Degree Palm Rotation" gesture 1002A, a "Zoom In/Out" command 116E is generated, and the camera performs the corresponding action 122. In some cases, the magnitude of N can correspond to a zooming magnitude, and the direction of the palm rotation can correspond to either a zoom in or zoom out action 122. For example, referring to FIG. 11, on-screen display 1100B illustrates a zooming function. The zoom screen 1100B has a "+" icon 1106 located on the right half of the screen, a "−" icon 1108 located on the left half of the screen, and a numerical zoom multiplier 1110. In this example, if a user (human 110) rotates her palm clockwise, the camera will perform a "Zoom In" action. If she rotates her palm counterclockwise, the camera will perform a "Zoom Out" action. If the second interpreter 106B classifies the electrical signals 126 as an "Intended Index Finger Flick Up" gesture 1002B, a "Take Photo OR Start/Stop Video" command 116F is generated, and the camera performs the corresponding action 122. If the second interpreter 106B classifies the electrical signals 126 as an "Index Finger Lift and Hold" gesture 1002C, a "Switch Between Camera and Video" command 116G is generated, and the camera performs the corresponding action. Referring to FIG. 11, in response to the "Switch Between Camera and Video" command 116G, an on-screen display affected by the camera may switch between screens 1100A and 1100B. In the active camera default screen 1100A, the crosshairs 1102 are circular. In the active video default screen 1100C, the crosshairs 1104 are rectangular, and a recording time indicator 1114 is displayed in the lower right hand corner of the screen 1100C. If the second interpreter 106 B classifies the electrical signals 126 as a "Fist Formation" gesture 1002D, a "Display Menu" command 116H is generated, and the camera performs the corresponding action. Referring to FIG. 11, in response to the "Display Menu" command 116H, an on-screen display affected by the camera may display menu screen 1100D containing menu 1112, enabling the user to control camera features such as brightness or flash. While certain predetermined gestures, predetermined actions, and correspondences between gestures and actions are described, any number or types of gestures, actions, and correspondences between gestures and actions that enable or assist the control of responsive devices may be used. For example, additional actions that enable or assist the control of a camera or a camera-compatible device may include swapping between cameras (e.g. swapping between a front and a rear camera), adding filters, and implementing augmented reality features such as Emojis.

Thus, the user (human 110) can provide input 114 to operate the camera (responsive device 112) without moving her hands toward the camera or touching the camera directly. Compared to user interfaces that require touching the camera, the user interface described here has the advantages of improved ergonomics, energy efficiency, and time savings, among other benefits. Furthermore, the user interface described in relation to FIG. 10 is compatible for applications where the camera may not be in reach of the user, such as cameras mounted on flying drones or remotely operated cameras.

Figure 6A:
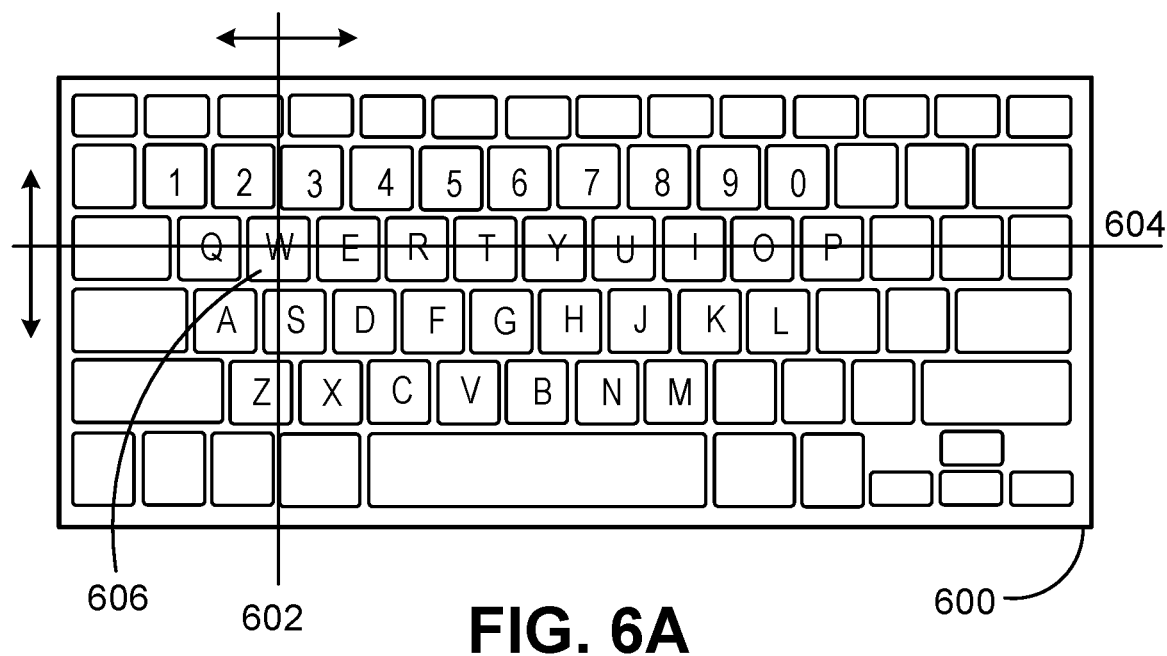

In some cases, a user interface such as the user interfaces 100 of FIGS. 1A and 1B can be used to replicate the functionality of user interface devices 102 such as real or virtual keyboards. FIG. 6A shows a virtual keyboard 600 that may be presented on an on-screen display of a responsive device 112. A vertical selector line 602 moves repeatedly back and forth between the left and right edges of the virtual keyboard 600, and a horizontal selector line 604 moves repeatedly up and down between the top and bottom edges of the virtual keyboard 600. To select a letter, a user can perform two index finger flicks up. The first index finger flick up generates nerve or other tissue electrical signals (input 114) that are interpreted to generate an output 116 to the responsive device 112 commanding it to stop the motion of the vertical selector line 602 (action 122) at a desired position that overlays a desired key. The second index finger flick up generates nerve or other tissue electrical signals (input 114) that are interpreted to generate an output 116 to the responsive device 112 commanding it to stop the motion of the horizontal selector line 604 (action 122) at a desired position that also overlays the desired key. Once the vertical selector line 602 and the horizontal selector line 604 are both stopped, the letter that is closest to the intersection 606 of the two lines is selected, and a key code representative of that letter is sent to the responsive device 112. The vertical selector line 602, the horizontal selector line 604, or both begin to move again, and the process is repeated.

Although FIG. 6A illustrates an alphanumeric QWERTY keyboard arrangement, a similar technique can be used for any kind of keyboard or any kind of arrangement of letters or numbers or other symbols to be chosen by user. Such a keyboard or other arrangement could be smaller, larger, of a different pattern or configuration, or include fewer or a greater number of letters, numbers, or symbols.

Figure 6B:
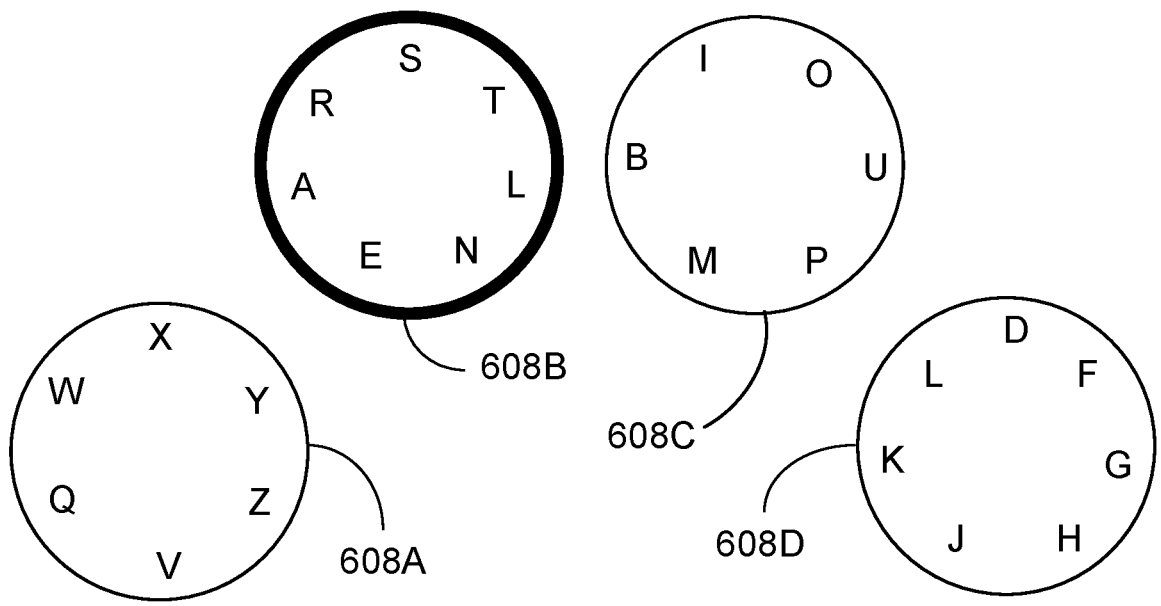

Referring to FIG. 6B, the functionality of a keyboard (user interface device 102) can be replicated using groupings of letters 608A-D that may appear on the on-screen display of a responsive device 112. Currently, the second grouping from the left 608B is selected as indicated by thickened borders. To select a letter, a user (human 110) can navigate to the grouping containing the desired letter by rotating his palm. This motion (input 114) is interpreted by the user interface 100 to generate an output 116 for the responsive device 112 commanding it to toggle through the other groupings in a similar fashion to the one described earlier. To select a grouping, the user can perform an index finger flick up. Once a grouping is selected, the user can toggle through the letters within the grouping by rotating his palm. To select a letter, the user can perform an index finger flick up. At any time, if the user desires to view all of the groupings 608A-D, he can rotate his palm 180 degrees so that it is facing upward and hold his palm in that position for a certain period of time, for example, for 1-3 seconds. Various groupings of letters 608A-D may be used. In some cases, letters may be grouped such that the most likely letters to be selected are organized in a manner that minimizes the expected amount of motion made by the user.

Figure 7A:
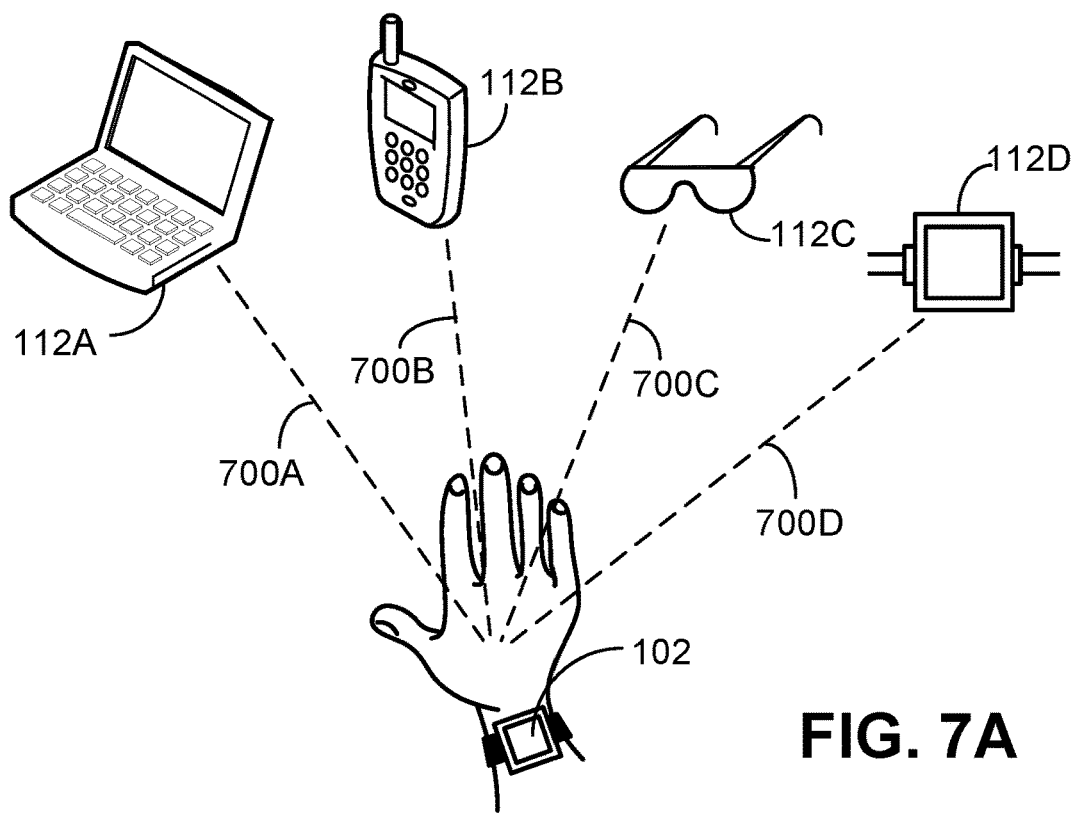

In some cases, a user interface such as the user interfaces 100 of FIGS. 1A and 1B may be used to operate multiple responsive devices 112A-D. Referring to FIG. 7A, a wrist-worn user interface device 102 may be capable of connecting wirelessly (e.g. via Bluetooth or other wireless communications within a frequency range of about 2400 MHz to about 2500 MHz) to a computer 112A, a smartphone 112B, a pair of smart glasses 112C, a smartwatch 112D, or one or more other devices, or combinations of them simultaneously or essentially simultaneously. In some cases, communicating to multiple responsive devices 112A-D can be managed using a Bluetooth round robin technique. In a Bluetooth round robin, the user interface device 102 interacts with each responsive device in turn for a set amount of time. For example, a Bluetooth connection 700A may first be established between the user interface device 102 and the computer 112A for one minute, allowing the user to operate the computer 112A. After one minute, the Bluetooth connection 700A is terminated, and a new Bluetooth connection 700B is established between the user interface device 102 and the smartphone 112B, allowing the user to operate the smartphone 112B. After another minute, the Bluetooth connection 700B is terminated, and a new Bluetooth connection 700C is established between the user interface device 102 and the smart glasses 112C, allowing the user to operate the smart glasses 112C. After another minute, the Bluetooth connection 700C is terminated, and a new Bluetooth connection 700D is established between the user interface device 102 and the smartwatch 112D, allowing the user to control the smartwatch 112D. Finally, after another minute, the Bluetooth connection 700D is terminated, a new Bluetooth connection 700A is established between the user interface device 102 and the computer 112A, and the cycle repeats itself. Although this example emphasizes Bluetooth connections, a similar round robin scheme can be implemented with wireless connections of any kind.

Figure 7B:
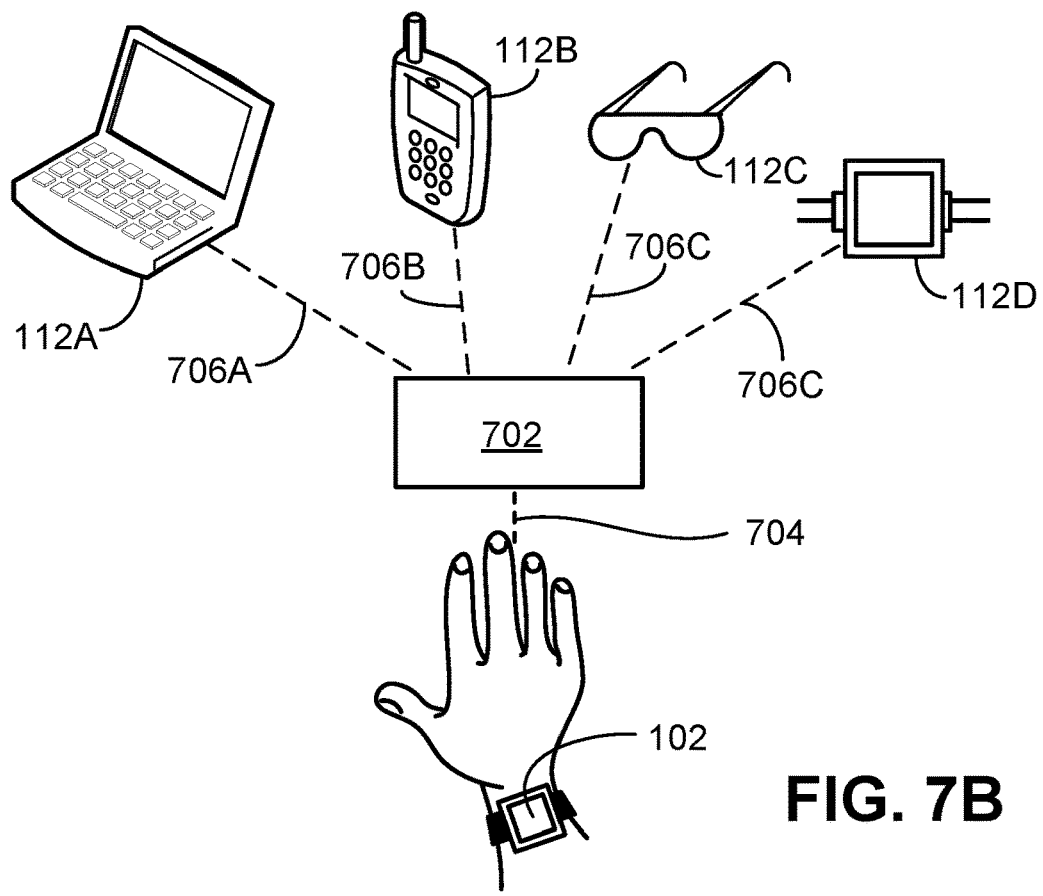
Figure 8:
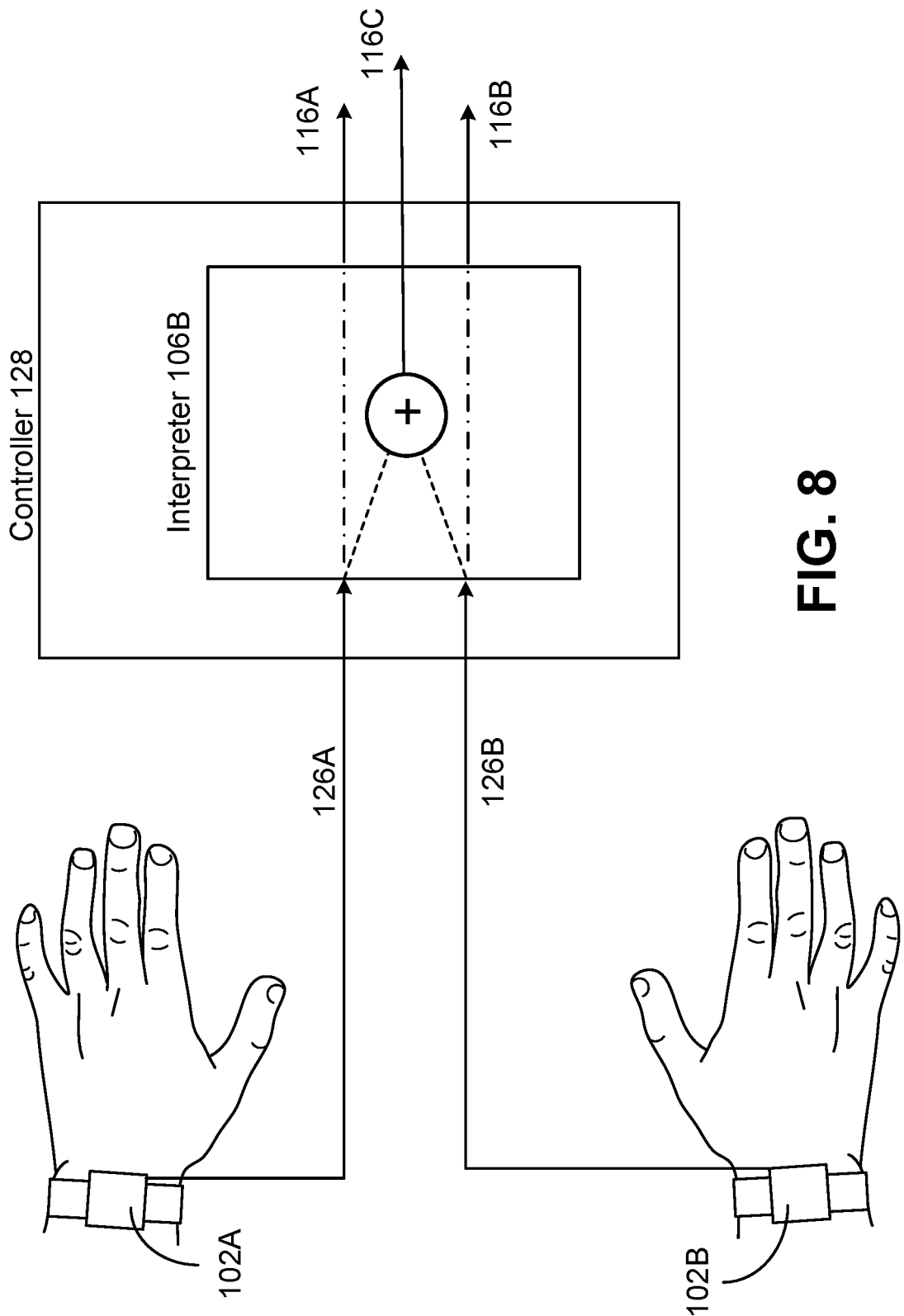

In some cases, communicating from a user interface to multiple responsive devices can be managed using an intermediary routing computing device 702, as shown in FIG. 7B. In this configuration, a user interface device 102 maintains a continuous wireless connection (e.g., a Bluetooth connection or other wireless connection communicating within a frequency range of about 2400 MHz to about 2500 MHz) to the intermediary routing computing device 702, and the intermediary routing computing device 702 is responsible for establishing and terminating connections 706A-D with the computer 112A, the smartphone 112B, the smart glasses 112C, and the smartwatch 112D, for example. In some instances, the intermediary routing computing device 702 can be configured always to prioritize a wireless connection 700A with the computer 112A over wireless connections 700B-D with the other devices 112B-D. In some examples, the intermediary routing computing device 702 can be configured to automatically establish a connection with the responsive device that is displaying the most recent notification. In an example, the user may be able to manually select which responsive device 112A-D he would like to connect to.

In some cases, the intermediary routing computing device 702 is capable of managing a variety of different wireless connections and data transfer protocols (e.g. UDP, TCP, etc.) that may be specific to each responsive device 112A-D. In such a configuration, the user interface device 102 only needs to establish one connection and one data transfer protocol with the intermediary routing computing device 702. Meanwhile, the intermediary routing computing device 702 handles forwarding the data or corresponding commands from the user interface device 102 according to the specific connection type and data transfer protocol of each responsive device 112A-D. For example, a user interface device 102 may send electrical signals 126 representative of nerve or other tissue electrical signals 114 to a smart speaker device (intermediary routing computing device 702). From there, the smart speaker device can manage connections to all other responsive devices 112A-D, either by forwarding the raw digitized electrical signals 126, higher level interpretations of the signals, or corresponding command outputs to one or more of the responsive devices 112A-D. This technique can be expanded such that some user interface configurations may include multiple intermediary routing computing devices 702, with each intermediary routing computing device 702 serving as a node in a mesh network. In such a configuration, raw digitized electrical signals 126, higher level interpretations of the signals, or corresponding command outputs can be distributed to a broader physical area than would be possible with a single direct Bluetooth, Wi-Fi, or other wireless connection.

In some applications, it may be possible to use a single user interface device to control two or more responsive devices simultaneously and without conflict by defining, for example, mutually exclusive easily distinguishable gestures to be applied specifically and only to corresponding respective responsive devices. For example, finger flicks could be used to control a computer display while palm rotations could be used simultaneously to control a robotic hand. In some applications, the two or more responsive devices being controlled simultaneously can have a shared user interface operated by the single user interface device. For example, the user interface device may be configured to select and drag media or files from one device to another, such as between two laptops, or between different devices like phones and televisions.

In some cases, a user interface such as the user interfaces 100 of FIGS. 1A and 1B may be distributed across two or more user interface devices 102. For example, referring to FIG. 8, a user (human 110) may be wearing two wrist-worn user interface devices 102A, 102B, each of which is able to generate electrical signals or data 126A, 126B representative of inputs 114 from the respective hand of a human 110. In some cases, the multiple user interface devices 102 may be distributed across multiple body parts or across multiple users. When the generated electrical signals or data 126A, 126B arrive at the second interpreter 106B of the controller 128, there are two possibilities for generating outputs 116 for the responsive device 112. In some cases, the electrical signals or data 126A, 126B are interpreted simultaneously as two discrete inputs, and two outputs 116A-B are generated for the responsive device 112 corresponding to the two discrete inputs. In some cases, the electrical signals or data 126A-126B are combined and interpreted as a joint input, generating a single output 116C for the responsive device. A variety of other arrangements would be possible to provide a robust, rich, deep, quick, easy facility for controlling a responsive device.

For example, if the user is wearing two wrist-worn user interface devices 102A-B and is using the user interface devices 102A-B to manipulate a music queue, she can control the volume of an audio track (output 116A) with one hand while selecting the next song (output 116B) with her other hand. This ability to multitask increases the efficiency of operating a responsive device 112 by allowing for more outputs to be generated for the responsive device 112 in the same amount of time.

In some cases, if the electrical signals or data 126A, 126B from the two wrist-worn user interface devices are combined to generate a single output 116C, a wider sample space of interpretations can be identified, allowing for a larger number of output options 116C to be generated for the responsive device.

Although the examples above referred to these two wrist-worn user interface devices, the two or more user interface devices could include a combination of any kind of user interface devices providing opportunities for even more subtle, complex, robust opportunities for controlling one or more responsive devices.

In some cases, the electrical signals or data 126A, 126B from one or more user interface devices 102A, 102B may be combined with electrical signals or data from sources other than user interface devices such as audio input from a human. Similar to the description given for FIG. 8, in some cases, the electrical signals or data 126A, 126B from the one or more user interface devices and the electrical signals or data from the other sources are interpreted simultaneously as two discrete inputs, generating two discrete outputs. In some cases, the electrical signals or data 126A, 126B from the one or more user interface devices and the electrical signals or data from the other sources are combined and interpreted as a joint input, generating a single output. For example, if the user is wearing a wrist-worn user interface device (e.g. 102A), she can simultaneously rotate her palm to control the zoom of a camera (generating electrical signals or data 126A from the wrist-worn user interface device 102A) and say the words "Take Photo" (audio input from the human) to cause the camera to take a photograph.

Although the examples above emphasize user interfaces 100 that include controllers 128 that perform high level interpretations to classify gestures (e.g. gestures 108A-C), it is understood, as described above, that in some cases, the controller 128 includes an interpreter 106B that performs lower level interpretations such as "Digitized Raw Signal" 108D, producing an output 116 substantially similar to received electrical signals 126. In the smart speaker example described in relation to FIG. 7B, the smart speaker (intermediary routing computing device 702), in some cases, simply forwards along the digitized raw signal received by user interface device 702 to responsive devices 112A-D. This configuration has the advantage of allowing each responsive device 112A-D to perform its own interpretations and actions based on the digitized raw (e.g. nerve or other tissue electrical) signal. In this example, the intermediary routing computing device is considered both a user interface device and a responsive device. It is a user interface device because it is an intermediary structure between a human and another responsive device, and it is also a responsive device because it performs an action (forwarding the digitized raw signal) upon receiving a corresponding input signal.

In some implementations, one or more sensors 124 within a given user interface device 102 are subjected to a calibration process at one or more times. For example, IMU sensors that track spatial and angular position and acceleration of an object may become inaccurate due to performing integration operations based on data collected at discrete moments in time. To reduce this inaccuracy, a reference point can be established that is independent of the position of the IMU. A calibration system that communicates wirelessly with the IMU (e.g., using wireless protocols or Bluetooth), can transmit values for the reference point, allowing the virtual vectors provided by the IMU to be computed against the real-world vectors provided by the calibration system. The IMU can be configured to recalibrate its position after a set number of spatial calculations or as commanded by the user or both.

In some cases, the user interfaces are configured to account for latency, for example varying delivery latency associated with wireless packet transmissions. To account for this variation, the electrical signals 126 representative of inputs 114 from the human 110, such as hand movements, can be signal processed on a time-variable basis. For example, if a first transmission packet (e.g. electrical signal 126) is delivered with a 10 ms latency and a second transmission packet is delivered with a 5 ms latency, the signal processing of the second transmission packet can be performed with a 5 ms delay to cause the temporal spacing of the output signals to be true to the original temporal spacing of the inputs 144 from the human 110.

In some examples, the user interfaces participate in applying security features to control the use of responsive devices in accordance with authorizations. For instance, such security features can be used to ensure that unauthorized users cannot operate responsive devices without permission. We sometimes use the term "authentication" and "verification" interchangeably to refer, for example, to determining the unique identity of a human or to the process of confirming whether the uniquely identified human has authorization to make full or partial control or use or a user interface device or a responsive device or both.

In some cases, data derived from nerve or other tissue electrical signals captured by a user interface device at the wrist in the course of normal activity (i.e., in a passive mode) or in the course of operating a responsive device (i.e., in a usage mode) can be used by an authentication process. In some instances, other kinds of data gathered by a wrist-worn device, such as data indicative of position and motion of the wrist, fingers, or arm, can be used in an authentication process. In some cases, nerve or other tissue electrical signals captured by the user interface device at the wrist can be combined with signals captured by one or more user interface devices at other parts of the body in an authentication process. The authentication process can be executed at specific times, such as when a human begins to use a user interface device or a responsive device, or at repeated times. In some instances, the verification process can be executed continuously in the context of ongoing operation of a user interface device or a responsive device. Authentication may be achieved by communication with a remote central server, by neighbor-to-neighbor communication in a mesh network, or other verification approaches, or combinations of them.

Figure 9:
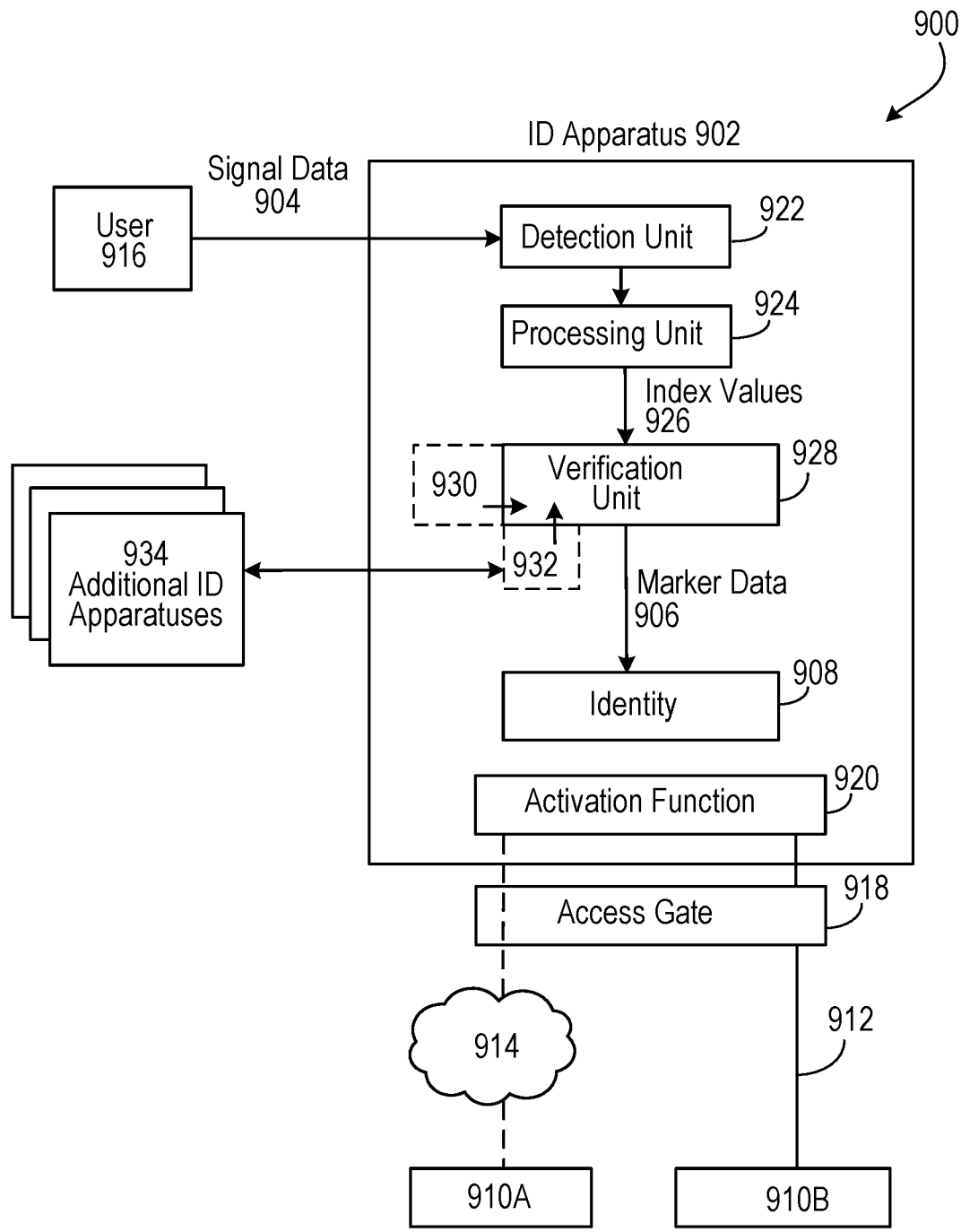

Referring to FIG. 9, in some implementations, a user authentication system 900 includes an identification apparatus (device) 902 for interpreting signals (signals or data or both 904) detected or received by the identification apparatus 902 as one or more markers (marker data 906) that uniquely denote or characterize an identity 908 of a particular human 916. The signals are data that can be received from one or more user interface devices or one or more responsive devices or other sources or combinations of them. For example, the signals can be received from one user interface device located on the user's wrist and a second user interface device located on the user's leg. The ID apparatus can use the markers to uniquely distinguish humans based on individual or sequential amplitude, pattern, timing, or length or combinations of them, of the detected or received signal or data. In some examples, the markers can be a binary system such as Morse code or can be a multidimensional system leveraging different signals or data, for example, from different sources on the human or can be analog amplitudes, timing, or length, or combinations of them, for example. The identification apparatus 902 can be connected electronically to one or more responsive devices or user interface devices or combinations of them 910A-B, whether physically or by software, communicating either directly 912 (paired mode) or through a remote server 914 (cloud-based mode) or both to control the use of the device based on results of the authentication process. The identification apparatus 902 may include an activation (authentication control) function 920 which, upon making a verification determination on the identity 908 of the human 916, can perform a variety of control functions to control access by the human through an access gate 918 to user interface devices or responsive devices 910A-B or to specific functions or features of the devices. In some cases, the access can be prevented if the verification determination was unsuccessful. In some instances, the access can be unlimited if the verification determination was successful. In some examples, the access can be limited with respect to time, location, context, or particular features or functions of the devices.

In some cases, a single verification of the identity 908 of the user 916 by the identification apparatus 902 can allow for control of multiple responsive devices (e.g., responsive devices 910A-B) without the need for any repeated verification. For example, upon the identification apparatus 902 verifying a user's identity 908 based on biometric signals (e.g., nerve or other tissue electrical signals) collected by a wrist-worn user interface device (e.g. user interface device 102), the user may then be allowed access to any number of responsive devices that he is authorized to use such as laptops, smart televisions, and mobile phones, for example, without the need to sign into (be authenticated for) each responsive device.

In some implementations, the signal or data 904 incorporates skin-surface-derived nerve or other tissue electrical activity signals or data, either in isolation or in combination with wrist acceleration or orientation, or other wrist position or motion information, or combinations of them, as measured by another sensor such as an inertial measurement unit (IMU). The signal data 904 and the marker data 906 may correspond to repeated, periodic, or discrete time intervals (or interval-based transformation) or may be derived from continuous signal or marker data, e.g., a continuous function operating in real-time or at multiple timescales. The signal data may be thresholded, normalized, or collected as raw data.

As the signal data 904 in a baseline or passive mode (with the user engaging in no activity) can be based on a combination of human finger, hand, and wrist morphology, body composition, and other factors, and as the signal data 904 generated during an active mode (with the user engaging in an activity that may include motion) involving either a responsive device 910A-B or the physical world includes additional elements of, for example, position, velocity, acceleration, three-dimensional orientation, interaction habits, and other features and information that are unique to a particular human, the signal data 904 (in raw form or transformed into marker data 906), represents a reliable and individualized marker (e.g., biomarker). Such a marker has a variety of practical applications, for example enabling unique authentication of a human as part of a login process when the human begins to make use of a user interface device or a responsive device as well as during ongoing interaction with or use of responsive devices 910A-B.

The signal data 904 may be collected in a passive mode (for example, when the user is wearing a user interface device but is not using and has no intention of operating a responsive device 910A-B). In some cases, signal data 904 may be collected during an active mode during activation of the responsive device 910A-B for the purposes of operating it (after the presentation of a specific prompt to the user to perform a sequence of gestures or temporally-arranged activations, whether in an isolated format or an interactive challenge/response format; or within an overlaid user interface interaction sequence).

The marker data 906 may be unique in isolation, with a one-to-one mapping of each marker data element to the identity 908 of each user 916, or may be analyzed for verification purposes in combination with other markers or in combination with other data (such as location, text, symbol, voice, fingerprints, or other information, or combinations of them) to create a unique combination marker (multifactor marker).

Any marker may be used by an authentication process for the verification of a wearer (user) identity 908 when implemented in either a primary (single) or multi-factor manner; for either discrete verification (as a method for implementing logins, for example) or to enable continuous (adaptive) access during use (as a method for implementation of real-time or retroactive access).

The identification apparatus may incorporate various software or hardware-based capabilities to perform on-board or remote-server-based processing of signal data (derived from the measurement of signals relating to, for example, the contraction or extension movement of one finger or multiple fingers, or the movement of the wrist in any axis, or the movement of the forearm along any axis; or any combination of them) into marker data as described below.

In some implementations, the identification apparatus 902 includes: a detection unit 922 which receives one or more nerve or other tissue electrical signals (signal data 904) from a surface-based IMU, from one or more electrodes, or from a combination of those sources; a processing unit 924 which calculates an index value 926 using received signals; and a verification unit 928 which stores index values 926 corresponding to pre-defined users 916 and calculates a marker value 906 from a thresholded algorithmic correspondence between index values 926 delivered from the processing unit 924 and the pre-stored index values of users. The processing unit 924 may expose the correspondence data electronically to external devices. The processing unit 924 and the verification unit 928 may be housed either in separate devices or together within the signal detection unit.

In some implementations, the verification unit 928 incorporates an on-board database apparatus 930 (or, in some cases, an apparatus linked electronically to a cloud-based server) which collects biometric and other marker data and which constitutes a resource serving (or transforming) user-level and aggregated signal data and marker data to the verification unit 928, or to other verification units.

In some instances, a curation unit 932 enables a single or multiple independent operators to activate, adjust, and monitor specified functions of the verification unit; by which the operator may accumulate, monitor, and remove selected index values (and other associated information) relating to pre-defined users; and by which sets or subsets of the users may be accorded differential access privileges by the operator, in real-time. Either one or multiple identification units 902 may be controlled in such a manner.

In some cases, the curation unit 932 which is housed on-board an identification apparatus 902 may transfer (on a push basis) selected signal data 904 or marker data 906 directly to other identification apparatuses 934, and store such data as transferred from other identification apparatuses 934, in order to facilitate a mesh-network-based or otherwise distributed collective verification scheme. In some instances, there can be a single central curation unit or server.

In some instances, the curation unit 932 incorporates a machine learning and classification system which allows for the development of methods of assigning markers 906 to signal data 904, as well as development of multifactor markers from existing marker data 906 and signal data 904.

User verification may be gated in combination with a method based on data including the location or proximity of the identification apparatus 902 to other verified users.

The signal data 904 and the marker data 906 may be exported from the curation unit 932 or a remote server, on an individual, aggregated, or anonymized basis for applications separate from verification purposes.

The signal data 904 and the marker data 906 may be used as activation cues for devices connected to the curation unit 932, a remote server, or another connected system.

When used in continuous mode, a change in the pattern of signal data 904 or marker data 906, as identified by the verification unit 928, may represent a trigger for the removal of access for a verified user, as a change in these data may be an indication of a change in the user 916 being served by the identification apparatus 902. The system 900 can be implemented as an exclusive authentication mechanism, or in conjunction with other authentication methods as refereed by the user interface or responsive device being server, for example. In some cases, in addition to authentication (e.g., biometric authentication) using signal data 904 and marker data 906, a user may be required to enter a passcode in order to have access to responsive devices 910A-B. Referring to FIG. 12, a user interface device can be used to enter the passcode for user authentication. In some cases, a responsive device (e.g. responsive devices 910A-B) may cause a locked password authentication screen 1200A to be presented on an on-screen display. A central lock icon 1202A depicts a closed padlock indicating that the user does not have access to operate the responsive device. In order to gain access, the user must enter a four-digit passcode. Similar to the example given with respect to selectable icons 202A-D in FIG. 2, to toggle between the different numerical digits, the user may rotate her palm clockwise or counterclockwise until the digit she intends to select is toggled for selection. To select a toggled digit, the user may perform an index finger flick up. If the user enters the correct four-digit passcode, an unlocked password authentication screen 1200B is presented on the on-screen display. On this screen 1200B, a central lock icon 1202B depicts an open padlock indicating that the user has access to operate the responsive device. If the user enters an incorrect four-digit passcode, the screen remains on locked password authentication screen 1200A and the user is prompted to try again. While the example given describes a four-digit numerical passcode, passcodes can be of any length and can comprise alphanumerical characters, shapes, pictures, or icons of any kind. In addition, while a palm rotation gesture and index finger flick up gesture are described as examples for entering a passcode, a wide variety of gestures and combinations of gestures and on-screen displays may be implemented to provide a passcode for user authentication.

As illustrated by the discussion and examples above, in some implementations, the inputs by a human user to a user interface that will be interpreted and then used to control, command, inform, or otherwise operate a responsive device can be one or more predetermined or predefined inputs such as motions, gestures or intentions. An interpreter is expecting to receive such an input, interpret it, and pass along to the responsive device a corresponding data, command, instruction, or guidance that will cause the responsive device to implement an action. In other words, the inputs and types of input that the interpreter can properly interpret and the corresponding actions and types of actions to be taken by the responsive device are prearranged. For example, when the user interface device is a wrist worn device that detects nerve or other tissue electrical signals corresponding to intended muscle contractions and extensions, and the responsive device is a computer display, certain gestures are predetermined as ones that the user should use and those gestures correspond to certain actions that the user interface devices predetermined to perform in response to corresponding predetermined gestures.

In some implementations, the predetermined gestures are chosen based on the capabilities, limitations, and other characteristics of the user interface device, the capabilities, limitations and other characteristics of inputs that the human is capable of or would find easy, natural, or intuitive to produce, the context in which the user interface device is used, the ability of an interpreter to interpret the gestures, and the capabilities, limitations and other characteristics of the user interface device that is to act based on the gestures, and other factors and combinations of them. The predetermined actions of the responsive device are chosen based on the capabilities, limitations, and other characteristics of the responsive device, the context in which the responsive device will act, and the relationship of the actions of the responsive device to corresponding capabilities, limitations, and other characteristics of the user interface device.

In particular applications of the technology that we have described, particular combinations of predetermined gestures of users through the user interface and predetermined corresponding actions of the responsive device are particularly effective, useful, or relevant to the context of the application. For example, the gesture of rotating the palm of the hand to cause a displayed object to rotate can be especially intuitive, useful, and effective.

Other implementations are within the scope of the following claims.

The invention claimed is:

1. A system for gesture-based control, the system comprising:
   a wearable device configured to be worn at a wrist of a person, the wearable device comprising:
      a biopotential sensor, the biopotential sensor being configured to detect biopotentials indicating a state of the hand of the person; and
      a wrist motion sensor, the wrist motion sensor being configured to obtain wrist motion data indicating a motion of the wrist;
      wherein the biopotential sensor is configured to output a first data stream, the first data stream being configured to indicate actions of the hand of the person; and
   a second device configured to output a second data stream, the second data stream also being configured to indicate the actions of the hand of the person;
   wherein the system is configured to:
   store first event data comprising (i) a plurality of biopotential data points from the first data stream and (ii) biopotential timestamps indicating a time that a respective biopotential data point was generated in the first data stream;
   store second event data comprising (i) one or more data points from the second data stream and (ii) one or more second device timestamps indicating when the one or more data points from the second device were generated in the second data stream;
   determine, based on an analysis of the second event data, that the hand of the person performed a first action;
   determine, based on the one or more second device timestamps, a first action time at which the first action occurred;
   based on the first action time and the biopotential timestamps, associate a label with a subset of the first event data, the label indicating that the first action occurred while the first event data was collected; and
   using at least the label and the first event data, train a machine learning interpreter to generate interpreted outputs based on at least biopotential data.

2. The system of claim 1, wherein the first action is desynchronized in the first event data as compared to the second event data, such that the first action occurs at earlier timestamps in the first event data than in the second event data.

3. The system of claim 2, wherein the first action occurs at least 30 milliseconds earlier in the first event data as compared to the second data.

4. The system of claim 2, wherein the first action occurs between 20 and 150 milliseconds earlier in the first event data as compared to the second data.

5. The system of claim 2, wherein, after determining the first action time based on the one or more second device timestamps, the system is configured to select the subset of the first event data to be associated with the label by analyzing the first event data in a time period that includes one or more biopotential data points having timestamps that precede the first action time determined based on the one or more second device timestamps.

6. The system of claim 1, wherein the second device comprises a physical button, and the second data stream indicates whether, at a given time, the person is pressing the physical button.

7. The system of claim 1, wherein the system is configured to display a game to the person while the first device collects the first data stream and the second device collects the second data stream, the game being configured to prompt the person to perform a series of actions that the machine learning interpreter will be trained to classify.

8. The system of claim 1, wherein the system is configured to, after an initial training of the machine learning interpreter based on the label and the first event data, update the machine learning interpreter based on data collected during continued simultaneous use by the person of the wearable device and the second device.

9. The system of claim 1, wherein the second device is not configured to be worn by the person.

10. The system of claim 1, wherein the second device is a physical mouse including a physical button.

11. A system for gesture-based control, the system comprising:
    a wearable device configured to be worn at a wrist of a person;
    a biopotential sensor, the biopotential sensor being configured to detect biopotentials indicating a state of the hand of the person;
    a wrist motion sensor, the wrist motion sensor being configured to obtain wrist motion data indicating a motion of the wrist;
    a machine learning interpreter configured to classify actions of the hand of the person, the machine learning interpreter being trained by a training process comprising:
    obtaining a first data stream comprising biopotential data;
    obtaining a second data stream comprising data generated by a second device;
    storing first event data comprising (i) a plurality of biopotential data points from the first data stream and (ii) biopotential timestamps indicating a time that a respective biopotential data point was generated in the first data stream;
    storing second event data comprising (i) one or more data points from the second data stream and (ii) one or more second device timestamps indicating when the one or more data points from the second device were generated in the second data stream;
    determining, based on an analysis of the second event data, that a first hand action was performed;
    determining, based on the one or more second device timestamps, a first action time at which the first hand action occurred;
    based on the first action time and the biopotential timestamps, associate a label with a subset of the first event data, the label indicating that the first hand action occurred while the first event data was collected; and
    using at least the label and the first event data, training the machine learning interpreter.

12. The system of claim 11, wherein the first hand action is desynchronized in the first event data as compared to the second event data, such that the first hand action occurs at earlier timestamps in the first event data than in the second event data.

13. The system of claim 12, wherein the first hand action occurs at least 30 milliseconds earlier in the first event data as compared to the second data.

14. The system of claim 12, wherein the first hand action occurs between 20 and 150 milliseconds earlier in the first event data as compared to the second data.

15. The system of claim 12, wherein the training process further comprises, after determining the first action time based on the one or more second device timestamps, selecting the subset of the first event data to be associated with the label by analyzing the first event data in a time period that includes one or more biopotential data points having timestamps that precede the first action time determined based on the one or more second device timestamps.

16. The system of claim 11, wherein the second device comprises a physical button, and the second data stream indicates whether, at a given time, the person is pressing the physical button.

17. The system of claim 11, wherein the training process further comprises displaying a game to the person while the first device collects the first data stream and the second device collects the second data stream, the game being configured to prompt the person to perform a series of actions that the machine learning interpreter will be trained to classify.

18. The system of claim 11, wherein the system is configured to, after an initial training of the machine learning interpreter based on the label and the first event data, update the machine learning interpreter based on data collected during continued simultaneous use by the person of the wearable device and the second device.

19. The system of claim 11, wherein the second device is not configured to be worn by the person.

20. The system of claim 11, wherein the second device is a physical mouse including a physical button.

* * * * *